US012797076B2

(12) United States Patent
Tanczos et al.

(10) Patent No.: US 12,797,076 B2
(45) Date of Patent: Nov. 17, 2026

(54) SYSTEMS, PROGRAMS AND METHODS FOR DETERMINING WHEN TO TERMINATE A CORONARY SINUS OCCLUSION TREATMENT

(71) Applicant: Miracor Medical SA, Awans (BE)

(72) Inventors: Jozef Tanczos, Uetikon am See (CH); Ventzeslav Iordanov, Valkenswaard (NL); Werner Mohl, Altenmarkt-Thennenberg (AT)

(73) Assignee: Miracor Medical SA, Awans (BE)

( * ) Notice: Subject to any disclaimer, the term of this patent is extended or adjusted under 35 U.S.C. 154(b) by 495 days.

(21) Appl. No.: 18/286,065

(22) PCT Filed: Apr. 8, 2021

(86) PCT No.: PCT/IB2021/052933
§ 371 (c)(1),
(2) Date: Oct. 6, 2023

(87) PCT Pub. No.: WO2022/214851
PCT Pub. Date: Oct. 13, 2022

(65) Prior Publication Data

US 2024/0215984 A1 Jul. 4, 2024

(51) Int. Cl.

| | |
|---|---|
| ***A61B 5/02*** | (2006.01) |
| ***A61B 5/0215*** | (2006.01) |
| ***A61B 17/12*** | (2006.01) |
| *A61B 17/00* | (2006.01) |

(52) U.S. Cl.
CPC .... *A61B 17/12122* (2013.01); *A61B 5/02028* (2013.01); *A61B 5/02152* (2013.01); *A61B 17/12136* (2013.01); *A61B 2017/00199* (2013.01)

(58) Field of Classification Search
None
See application file for complete search history.

(56) References Cited

U.S. PATENT DOCUMENTS

| | | | |
|---|---|---|---|
| 9,855,049 | B2 | 1/2018 | Schiemanck et al. |
| 2004/0172004 | A1 | 9/2004 | Mohl |
| 2013/0282042 | A1 | 10/2013 | Mohl |
| 2021/0077792 | A1 | 3/2021 | Kapur et al. |

FOREIGN PATENT DOCUMENTS

| | | | |
|---|---|---|---|
| CN | 105792761 | A | 7/2016 |
| CN | 104185492 | B | 12/2016 |
| WO | 2013/093576 | A1 | 6/2013 |

OTHER PUBLICATIONS

Notification of First Office Action issued in CN application No. 202180001267.0, mailed Oct. 29, 2023. English translation included.
Search Report issued in Cn application No. 2021800012670, dated Oct. 28, 2023. English translation included.

*Primary Examiner* — Deborah L Malamud
(74) *Attorney, Agent, or Firm* — Barnes & Thornburg LLP

(57) ABSTRACT

A system includes a coronary sinus occlusion device operable to occlude at least a portion of a coronary sinus of a heart of a patient, and a control system that activates the coronary sinus occlusion device and generates a user prompt on a user interface to terminate a coronary sinus occlusion treatment in response to a detected condition.

16 Claims, 10 Drawing Sheets

SYSTEMS, PROGRAMS AND METHODS FOR DETERMINING WHEN TO TERMINATE A CORONARY SINUS OCCLUSION TREATMENT

CROSS-REFERENCE TO RELATED APPLICATION

This application is a US 371 National Phase Application from PCT/IB2021/052933 filed Apr. 8, 2021, the disclosure of which is hereby incorporated by reference.

TECHNICAL FIELD

This disclosure relates to a system for treating heart tissue and related methods.

BACKGROUND

The heart muscle receives arterial blood via coronary arteries so that the blood passes through and nourishes the heart muscle tissue. In some cases, a blockage in a coronary artery can result in a loss or reduction of blood flow through a portion of the heart muscle (myocardium), thereby creating an area of ischemic damage, often leading to microcirculatory dysfunction. The injury of the ischemic heart muscle tissue can also be exacerbated by reperfusion injury from a sudden reperfusion of blood to tissue that had been deprived of adequate blood flow. After the blockage is removed or otherwise opened to resume blood flow, the ischemic portion of the heart muscle tissue (such as the reperfused microcirculation) can be damaged to the point that normal blood flow does not return through the ischemic portion of the muscle tissue.

Some conventional systems attempt to repair or treat the ischemic heart muscle tissue by supplying the ischemic tissue, for example, with blood through retrograde perfusion. In another example, the coronary sinus can be temporarily occluded so that the blood therein counterflows back from the coronary sinus through the coronary venous system and toward the ischemic muscle tissue that previously did not receive blood from the arterial side. The occlusion of the coronary sinus causes a pressure increase and, as a result, a redistribution of venous blood via the respective vein(s) into the capillaries of the border-zone ischemic muscle tissue to improve the blood supply to that ischemic area. In addition, the pressure increase translates through non-deprived areas of the microcirculation into increase in arterial pressure and activates collateral flow and release of vasoactive molecules. When the occlusion is ceased so that blood exits normally through the coronary sinus, the venous blood is flushed out while the metabolic waste products and the debris from the damaged tissue are carried off at the same time.

The combination of repeated venous pressure build-up phases followed by a phase of redistribution of flow and wash-out, often referred to as an intermittent coronary sinus occlusion ("ICSO") method, might in some circumstances improve arterial blood demand, improve microcirculation by reducing microvascular obstructions, provide a cardioprotective effect, and reduce ischemic tissue infarct size. When the timing of the ICSO method (e.g., the occlusion times and the release times) is controlled based upon monitored pressure measurements distal to occlusion, the method is often referred to as pressure-controlled ICSO, or "PiCSO." A computer-implemented control system can be used to control the timing of when to start and when to end, and hence the duration of, the occlusion phases that are performed during a PiCSO method.

SUMMARY

This disclosure relates to processes and systems for treating heart tissue, e.g., myocardium, that can include a control system and catheter device operated in a manner to intermittently and repeatedly occlude the coronary sinus or any of its attributes for the treatment duration to improve microcirculatory function within the treated heart tissue. Various implementations described in this disclosure can include optimally treating a patient over an optimal treatment duration by controlling the coronary sinus occlusion treatment administered to treat ischemic or otherwise damaged heart muscle tissue and its duration by determining, in real time, when to recommend terminating or when to terminate the coronary sinus occlusion treatment. The coronary sinus occlusion treatment can involve multiple, intermittent occlusion phases in which the coronary sinus is occluded by a coronary sinus occlusion device. The processes and systems provided herein can use measured values to establish parameters, such as a coronary sinus pressure, calculated by the described algorithm to determine an optimal timing to end the treatment period. In addition to the pressure-controlled intermittent coronary sinus occlusions during the treatment, cycles with predetermined duration might be added to optimize the algorithm.

In one aspect, a system includes a coronary sinus occlusion device operable to occlude at least a portion of a coronary sinus of a heart of a patient, and a control system connectable to the coronary sinus occlusion device and configured to execute computer-readable instructions that perform operations. The operations include activating the coronary sinus occlusion device to intermittently occlude the coronary sinus during a plurality of occlusion phases of a coronary sinus occlusion treatment, operating the coronary sinus occlusion device to release each intermittent occlusion of the coronary sinus during the coronary sinus occlusion treatment, receiving sensor data signals indicative of a hemodynamics parameter of the heart during the plurality of occlusion phases, comparing a threshold value to an indicator value that is based on the sensor data signals of the plurality of occlusion phases, and terminating the coronary sinus occlusion treatment based on said comparing the threshold value to the value or providing a user prompt on a user interface to terminate the coronary sinus occlusion treatment based on said comparing the threshold value to the indicator value.

In another aspect, a system includes a coronary sinus occlusion device operable to occlude at least a portion of a coronary sinus of a heart of a patient, and a control system that activates the coronary sinus occlusion device and generates a user prompt on a user interface to terminate a coronary sinus occlusion treatment in response to a detected condition.

In another aspect, one or more non-transitory computer readable media is featured. The one or more non-transitory computer readable media stores instructions executable by one or more processing devices, and upon such execution cause the one or more processing devices to perform operations. The operations include operating a coronary sinus occlusion device to intermittently occlude a coronary sinus of a heart during a plurality of occlusion phases of a coronary sinus occlusion treatment, operating the coronary sinus occlusion device to release each intermittent occlusion during the coronary sinus occlusion treatment, receiving sensor data signals indicative of a hemodynamics parameter of the heart during the plurality of occlusion phases, comparing a threshold value to an indicator value that is based on the sensor data signals of the plurality of occlusion phases, and terminating the coronary sinus occlusion treatment based on said comparing the threshold value to the value or providing a user prompt on a user interface to terminate the coronary sinus occlusion treatment based on said comparing the threshold value to the indicator value.

In another aspect, a method includes operating a coronary sinus occlusion device to intermittently occlude a coronary sinus of a heart during a plurality of occlusion phases of a coronary sinus occlusion treatment, operating the coronary sinus occlusion device to release each intermittent occlusion during the coronary sinus occlusion treatment, receiving sensor data signals indicative of a hemodynamics parameter of the heart during the plurality of occlusion phases, and terminating the coronary sinus occlusion treatment in response to comparing a threshold value to a value that is based on the sensor data signals of a plurality of occlusion phases.

In another aspect, one or more non-transitory computer readable media is featured. The one or more non-transitory computer readable media stores instructions executable by one or more processing devices, and upon such execution cause the one or more processing devices to perform operations. The operations include receiving data indicative of values of a hemodynamics parameter in a coronary sinus during a plurality of occlusion phases of a coronary sinus occlusion treatment, determining that the values of the hemodynamics parameter are substantially in steady state, and providing a user prompt to terminate the coronary sinus occlusion treatment in response to determining that the values are of the hemodynamics parameter are substantially in steady state.

In another aspect, a method includes receiving data indicative of values of a hemodynamics parameter in a coronary sinus during a plurality of occlusion phases of a coronary sinus occlusion treatment, determining that the values of the hemodynamics parameter are substantially in steady state, and providing a user prompt to terminate the coronary sinus occlusion treatment in response to determining that the values are of the hemodynamics parameter are substantially in steady state.

In another aspect, one or more non-transitory computer readable media is featured. The one or more non-transitory computer readable media stores instructions executable by one or more processing devices, and upon such execution cause the one or more processing devices to perform operations. The operations include receiving data indicative of values of a hemodynamics parameter in a coronary sinus during a plurality of occlusion phases of a coronary sinus occlusion treatment, predicting, based on the values of the hemodynamics parameter, a value of the hemodynamics parameter, and providing a recommended duration for the coronary sinus occlusion treatment based on the values of the hemodynamics parameter and the predicted value of the hemodynamics parameter.

In another aspect, a method includes receiving data indicative of values of a hemodynamics parameter in a coronary sinus during a plurality of occlusion phases of a coronary sinus occlusion treatment, predicting, based on the values of the hemodynamics parameter, a value of the hemodynamics parameter, and providing a recommended duration for the coronary sinus occlusion treatment based on the values of the hemodynamics parameter and the predicted value of the hemodynamics parameter.

Implementations can include one or more of the features described below or elsewhere in this disclosure.

In some implementations, a coronary sinus occlusion device can be used to perform the coronary sinus occlusion treatment.

In some implementations, the coronary sinus occlusion device includes an expandable member insertable into the coronary sinus and expandable to occlude at least the portion of the coronary sinus, and a sensor that generates the sensor data signals. In some implementations, the sensor is positioned near the expandable member. In some implementations, the coronary sinus occlusion device includes a catheter, and the expandable member and the sensor are positioned on a distal portion of the catheter. In some implementations, the sensor is a pressure sensor configured to measure a pressure or a rate of change of the pressure in the coronary sinus. In some implementations, the sensor is configured to measure a flow rate in a coronary artery of the patient or a rate of change of the flow rate in the coronary artery of the patient, a flow rate in a coronary venous system distal to a distal end of the coronary sinus occlusion device or a rate of change of the flow rate in the coronary venous system, a coronary wedge pressure associated with the coronary sinus occlusion device or a rate of change of the coronary wedge pressure, a density or viscosity of blood in the coronary venous system or a rate of change of the density or viscosity, a temperature of a fluid injected into a coronary sinus of the patient or a rate of change of the temperature of the fluid, a quantitative flow ratio of microcirculation or a rate of change of the quantitative flow ratio, a microvascular resistance in the coronary sinus or a rate of change of the microvascular resistance, or any combination thereof.

In some implementations, the sensor is a first sensor, the sensor data signals are first sensor data signals, and the coronary sinus occlusion device further includes a second sensor configured to generate second sensor data signals indicative of a pressure or a rate of change of the pressure in the coronary sinus, and the indicator value is based on the first sensor data signals and the second sensor data signals.

In some implementations, the coronary sinus occlusion device includes an expandable member insertable into the coronary sinus and expandable to occlude at least the portion of the coronary sinus, a first sensor that generates at least some of the sensor data signals, and a second sensor that generates at least some of the sensor data signals, wherein the first and second sensors are positioned on first and second sides of the expandable member.

In some implementations, receiving the sensor data signals includes receiving, from a sensor configured to measure the hemodynamics parameter in an arterial system of the heart, the sensor data signals.

In some implementations, the sensor data signals are indicative of a pressure or a rate of change of the pressure in the coronary sinus. In some implementations, the operations or method include determining the indicator value based on, for each of the plurality of occlusion phases, a maximum value of the pressure or the rate of change of the pressure in the coronary sinus in a period of time during a corresponding occlusion phase. In some implementations, the period of time corresponds to an end period of the corresponding occlusion phase. In some implementations, the end period includes a duration of 0.5 seconds to 3 seconds. In some implementations, the operations or method include determining the indicator value based on, for each of the plurality of occlusion phases, an average value of the pressure or the rate of change of the pressure in the coronary sinus in a period of time during a corresponding occlusion phase.

In some implementations, said terminating the coronary sinus occlusion treatment or providing the user prompt on the user interface to terminate the coronary sinus occlusion treatment is performed in response to a determination that a plurality of indicator values that are based on the sensor data signals of the plurality of occlusion phases are substantially in steady state, the plurality of indicator values including the indicator value. In some implementations, the operations or method include predicting a value of the hemodynamics parameter. The indicator value can correspond to a difference between at least one of the plurality of indicator values and the predicted value. In some implementations, the at least one of the plurality of indicator values corresponds to a last indicator value of the plurality of indicator values. In some implementations, said predicting the value of the hemodynamics parameter includes computing a logarithmic fit based on the plurality of indicator values. In some implementations, the difference is a percent difference between the at least one of the plurality of indicator values and the predicted value. In some implementations, the threshold value is no less than 1 percent and is no more than 5 percent. In some implementations, the operations or method include determining the threshold value based on one or more of a condition of the patient or a type of the coronary sinus occlusion treatment.

In some implementations, the operations include after providing the user prompt on to terminate the coronary sinus occlusion treatment, terminating the coronary sinus occlusion treatment only if at least a duration of the coronary sinus occlusion treatment is no less than a threshold duration.

In some implementations, the operations include determining indicator values that are based on the sensor data signals during an occlusion phase of the plurality of occlusion phases. The indicator values can include the indicator value. Termination of the occlusion phases of the coronary sinus occlusion treatment can be based on the indicator values during the occlusion phase.

Some or all of the implementations detailed below may provide one or more of the following advantages. First, some implementations of the systems and processes described herein can determine an optimal amount of time for a coronary sinus occlusion treatment by determining, based on at least real-time data, when to terminate the coronary sinus occlusion treatment.

Second, in particular implementations, the systems and processes can also provide clinicians and other healthcare professionals with both measured and predicted information related to the course of treatment, such as a predicted duration of the treatment.

Third, in some implementations described herein, both health care providers and patients being treated can benefit from the systems and methods described in this disclosure, which can determine an appropriate treatment duration and control administration of the treatment during that determined duration. In some cases, the systems and methods provided in this disclosure can determine a treatment time that is shorter than expected, thereby reducing the time needed for constraining the patient to medical monitoring equipment or a limited area. In addition, these systems and methods can allow the health care provider to care for and use the medical monitoring equipment for other patients in need. In some cases, the systems and methods can determine that the treatment time should be longer than expected in order to yield a health benefit, such as inducing microcirculation within the heart tissue being treated, that might have otherwise not been achieved with a shorter treatment duration. Thus, an increased clinical benefit and improved health condition may be achieved with an optimal treatment duration.

Fourth, in some implementations, the methods and systems provided in this disclosure can also advantageously provide an individualized treatment duration based on at least physiological vitals detected from each patient being treated. The optimal treatment duration may not be the same for each individual. Thus, the optimal duration can be varied depending on the health condition, age, other factors associated with the individual being treated to yield a clinical benefit and an improved health condition. As a result, shortening of the vulnerable period can be achieved.

The details of one or more implementations of the subject matter described in this disclosure are set forth in the accompanying drawings and the description below. Other potential features, aspects, and advantages will become apparent from the description, the drawings, and the claims.

DETAILED DESCRIPTION

Figure 1:
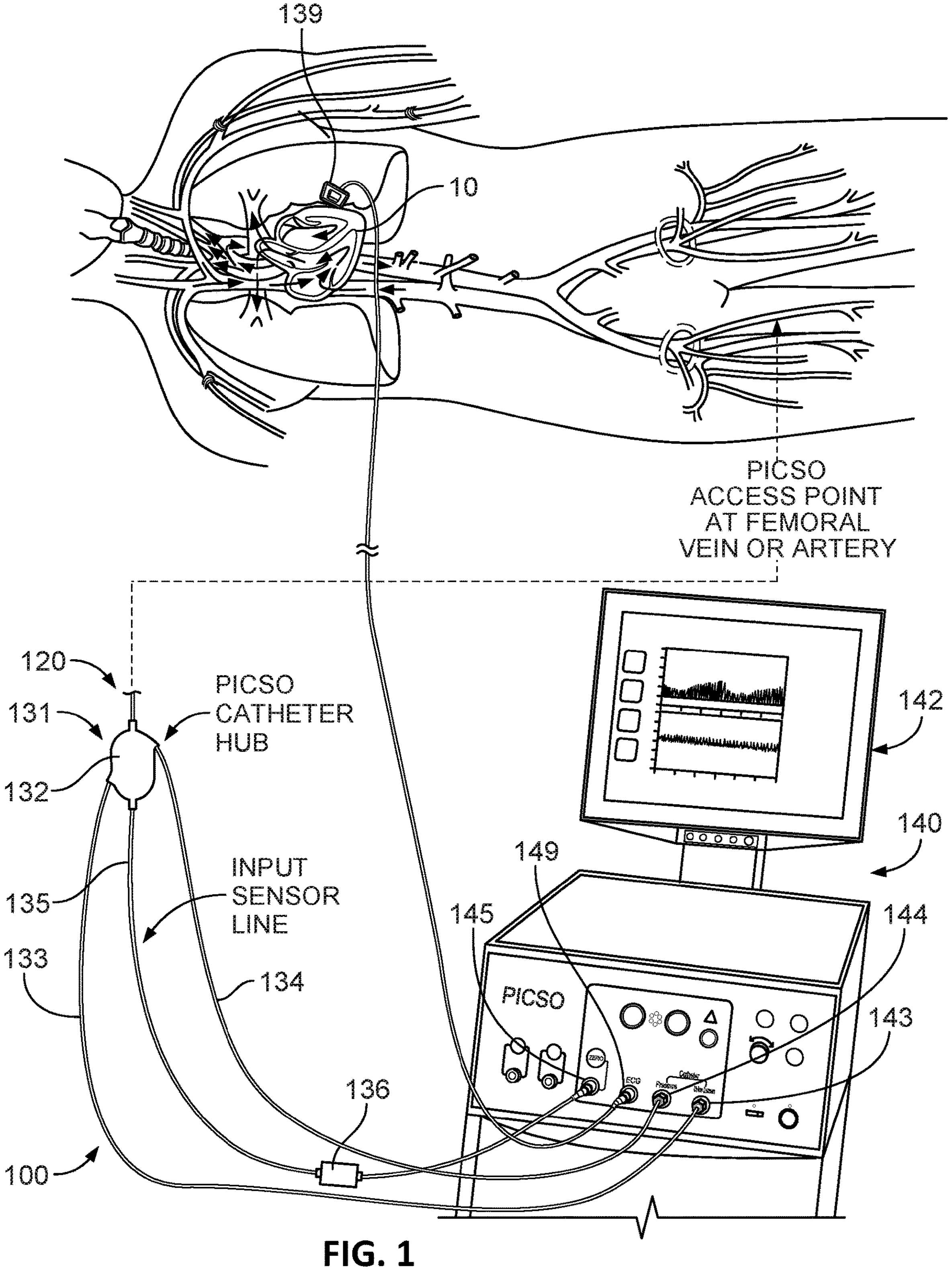
FIG. 1 is a schematic of a heart treatment system performing an operation on a patient.

Referring to FIG. 1, some implementations of a heart treatment system 100 for treating heart tissue can include a coronary sinus occlusion device 120 operable to occlude at least a portion of a coronary sinus 20 (FIG. 2) of a heart 10. For example, at least a portion of the coronary sinus occlusion device 120 is positionable near or at the coronary sinus 20 (FIG. 2) of the heart 10, and can be activated to occlude the portion of the coronary sinus 20 and can be deactivated to release the occlusion. A control system 140 is configured to operate the coronary sinus occlusion device 120 and can, in particular, operate the coronary sinus occlusion device 120 to intermittently occlude the coronary sinus 20 of the heart 10. During a coronary sinus occlusion treatment performed by the system 100, the occlusion of the coronary sinus can intermittently occur over multiple occlusion phases, each of which is followed by a corresponding release phase in which the coronary sinus occlusion device 120 is released from the coronary sinus 20. Furthermore, during the coronary sinus occlusion treatment, the control system 140 can receive one or more sensor signals that provide data indicative of a hemodynamics parameter. The control system 140 can terminate the coronary sinus occlusion treatment based on at least the one or more sensor signals. As discussed in this disclosure, the determination of the termination of the coronary sinus occlusion treatment can involve comparing a threshold value to a determined indicator value that is computed based on at least the one or more sensor signals. By terminating the coronary sinus occlusion treatment based on at least this comparison, the control system 140 can verify that the coronary sinus occlusion treatment is improving heart function and can decrease a required duration of the treatment.

Example Systems

Figure 2:
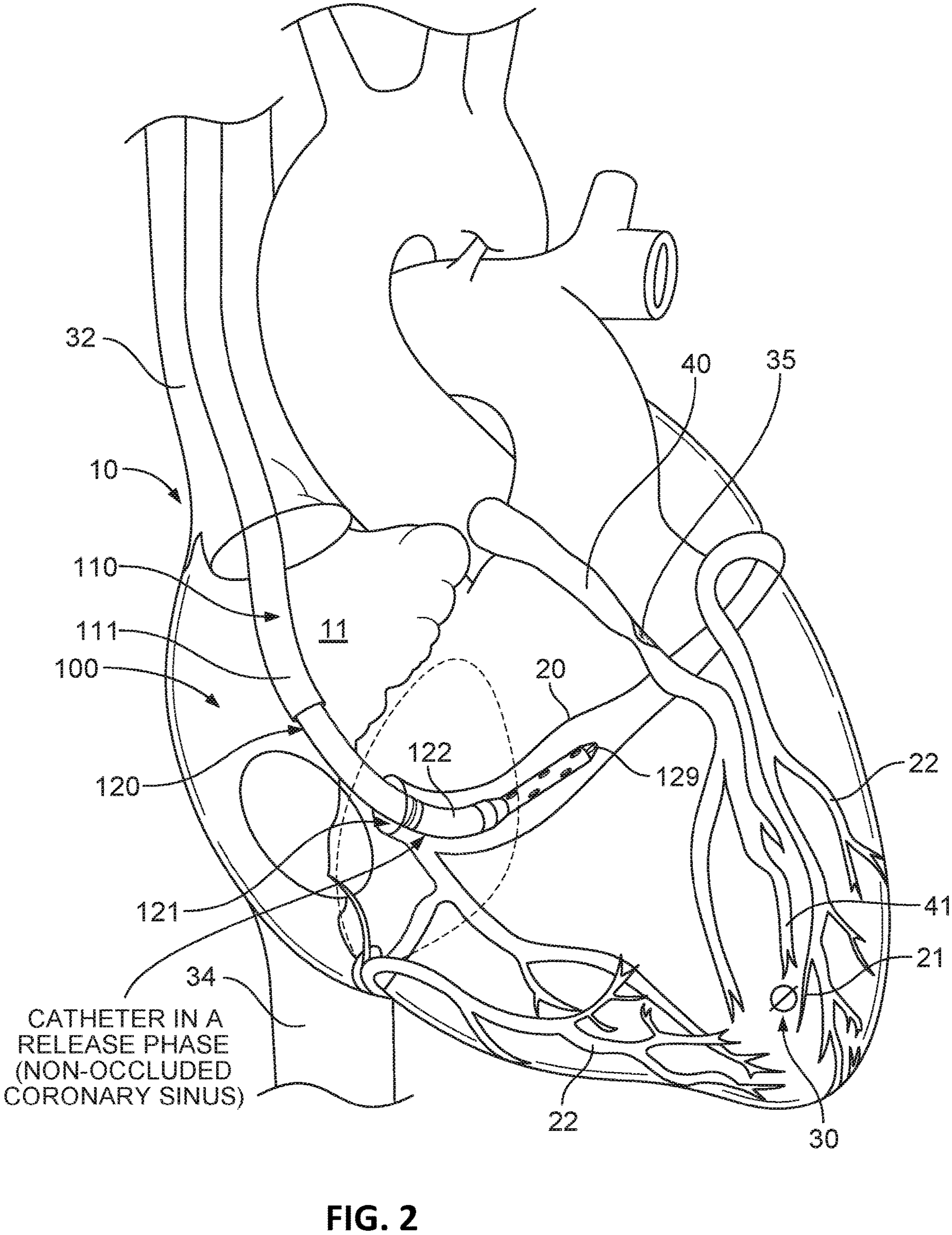
FIGS. 2-3 are anterior views of a heart with a portion of a coronary sinus occlusion device in a heart.
Figure 3:
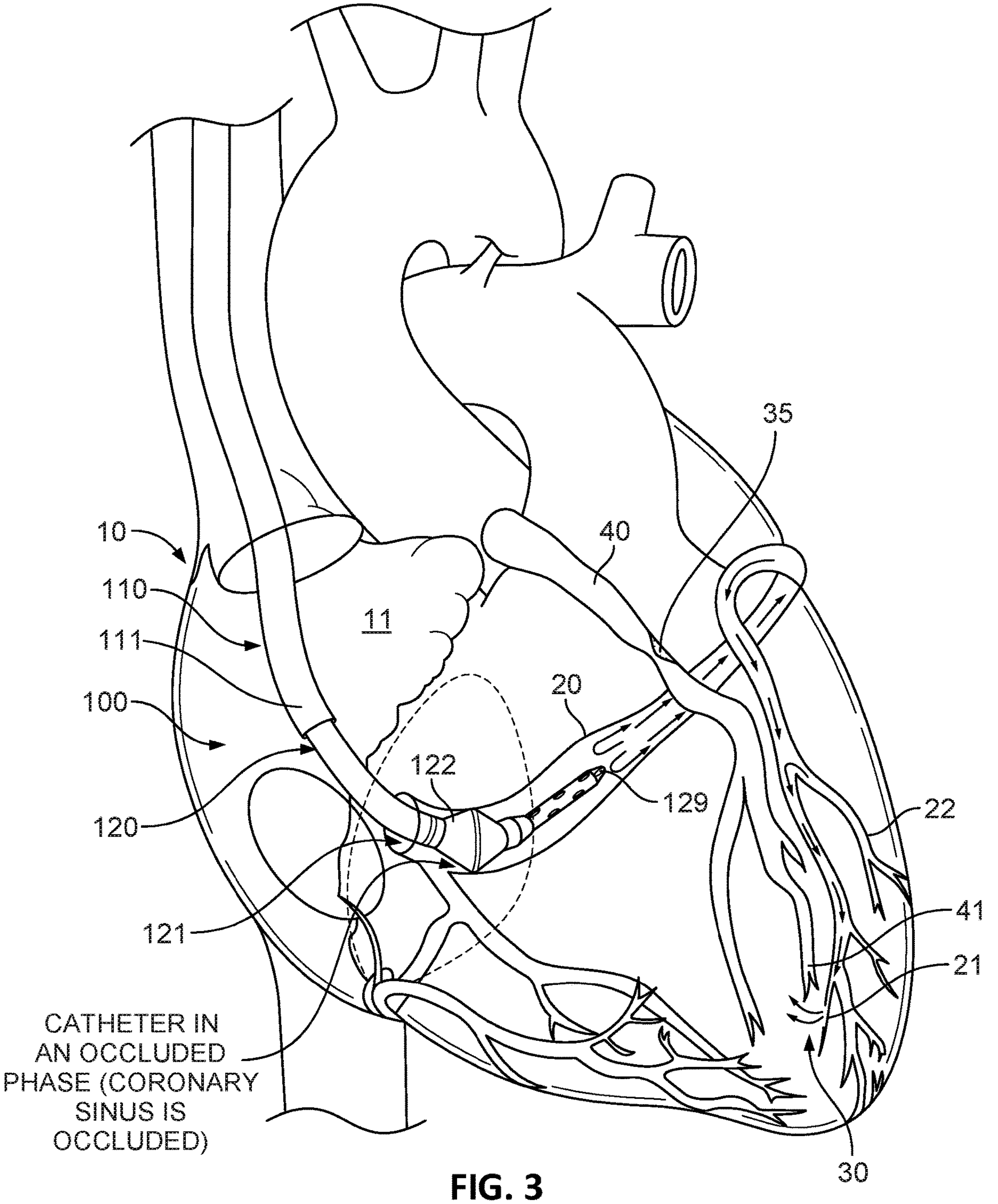
Figure 4:
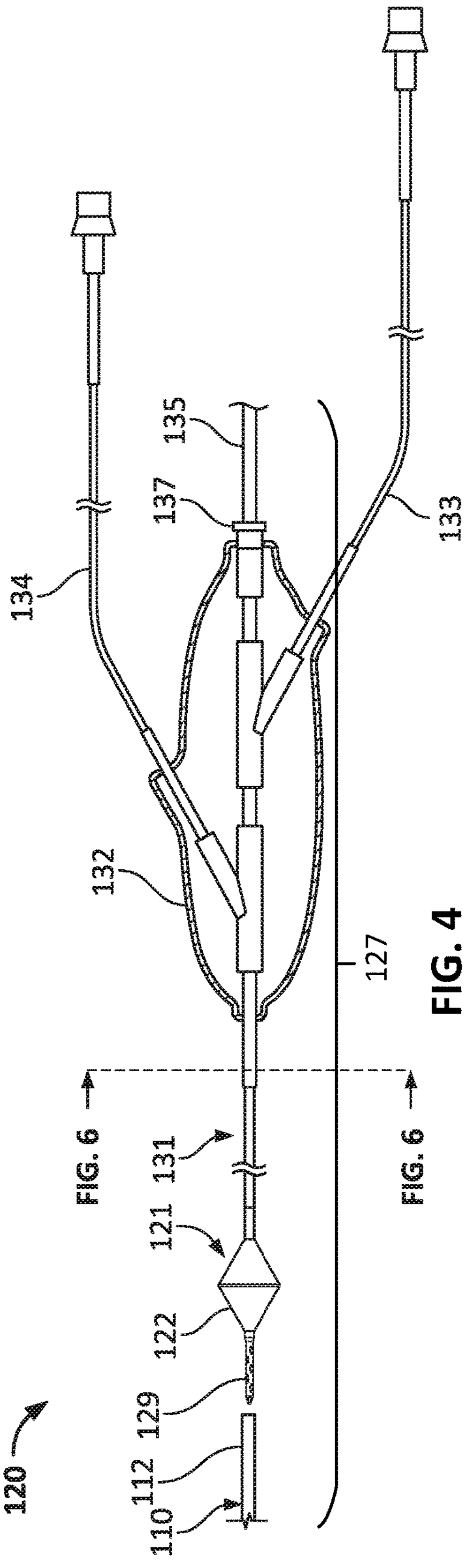
FIG. 4 is a front view of a coronary sinus occlusion device and a guide member for the coronary sinus occlusion device.

Referring to FIGS. 2-4, a heart treatment system 100 is operatively connected to a coronary sinus occlusion device 120 during a coronary sinus occlusion treatment. The coronary sinus occlusion device 120 is insertable into a guide member 110 so that a distal portion 121 of a catheter 127 (FIG. 4) of the coronary sinus occlusion device 120 can be positioned in the coronary sinus 20 of the heart 10.

The system 100 can optionally include a guide member 110 that is advanced through the venous system of the patient and into the right atrium 11. In some implementations, the guide member 110 includes a guide sheath having a lumen extending between a distal end 111 (FIG. 2) and a proximal end 112 (FIG. 4). The guide member 110, in other implementations, can provide guidance for a guide wire having an exterior surface extending between the distal end and the proximal end. The guide member 110 can include a steerable mechanism to control the orientation of the distal end to steer the distal end 111 through the venous system and into the right atrium 11. The steerable mechanism can be manually operable by a user or can be operable by the control system 140. The guide member 110 can include one or more marker bands along the distal end 111 so that the position of the distal end can be monitored during advancement using an imaging device.

The coronary sinus occlusion device 120 is configured to have a non-occluding position (FIG. 2) when the coronary sinus occlusion device 120 is activated and an occluding position (FIG. 3) when the coronary sinus occlusion device 120 is deactivated. The coronary sinus occlusion device 120 is operable to intermittently occlude the coronary sinus during a coronary sinus occlusion treatment and thereby redistribute venous blood flow toward heart muscle tissue 30. In the non-occluding position (FIG. 2), one or more components of the distal portion 121 can be operated to place the coronary sinus occlusion device 120 in the occluding position (FIG. 3) to occlude the coronary sinus 20.

Referring generally to FIGS. 1-4, the control system 140 (FIG. 1) is configured to operate the coronary sinus occlusion device 120 during a coronary sinus occlusion treatment that includes intermittent occlusion phases in which the coronary sinus occlusion device 120 is in the occluding position (FIG. 3), each of which is followed by a corresponding release phase in which the coronary sinus occlusion device 120 is in the non-occluding position (FIG. 2).

As a general matter, in a process for positioning the coronary sinus occlusion device 120 in the coronary sinus 20 and for administering a coronary sinus occlusion treatment, the guide member 110 is inserted through the venous system of a patient and into the right atrium 11. After the guide member 110 is advanced into the right atrium 11, the distal end 111 of the guide member 110 can be temporarily positioned in the coronary sinus 20 or the coronary sinus ostium.

From there, the catheter 127 (FIG. 4) of the coronary sinus occlusion device 120 can be inserted into the guide member 110, thereby slidably advancing the distal portion 121 of the coronary sinus occlusion device 120 along the guide member 110 for positioning the distal portion 121 inside the coronary sinus 20. In implementations in which the guide member 110 includes a guide sheath, the distal portion 121 of the coronary sinus occlusion device 120 can slidably engage with an interior surface of the lumen during advancement toward the coronary sinus 20. In some implementations in which the guide member 110 includes a guide wire structure, the distal portion 121 of the coronary sinus occlusion device 120 can slidably advance over the exterior surface of the guide wire during advancement toward the coronary sinus 20. For example, a lumen 125 of the coronary sinus occlusion device 120 can pass over the guide wire structure. In the example shown in FIG. 2, the guide member 111 and the coronary sinus occlusion device 120 are inserted into the right atrium 11 through the superior vena cava 32. In other implementations, the guide member 111 and the coronary sinus occlusion 120 are inserted into the right atrium 11 through the inferior vena cava 34.

After the coronary sinus occlusion device 120 reaches the coronary sinus 20, the distal end 111 of the guide member 110 can be withdrawn and remain in a position within the ostium of the coronary sinus or in the right atrium 11 for mechanical support during use of the coronary sinus occlusion device 120. The coronary sinus occlusion device 120 is inserted while the coronary sinus occlusion device is in the non-occluding position (FIG. 2). As a result, when the coronary sinus occlusion device 120 reaches the coronary sinus 20, the coronary sinus occlusion device 120 is in the non-occluding position (FIG. 2).

When the coronary sinus occlusion device 120 is positioned in the coronary sinus 20, the coronary sinus occlusion device 120 can be intermittently activated to administer the coronary sinus occlusion treatment. When the coronary sinus occlusion device 120 is in the occluding position (FIG. 3), the venous blood flow that is normally exiting from the coronary sinus 20 can be redistributed into a portion of heart muscle tissue 30 that has been damaged due to blood deprivation in microcirculation (and or collateral flow) and myocardium or loss of functional myocardium. For example, the portion of heart muscle tissue 30 can suffer from a lack of blood flow due to a blockage 35 in a coronary artery, or subsequent injury as described in the background 40. As a result, the arterial blood flow to the affected heart muscle tissue 30 via a local artery 41 can be substantially reduced such that the heart muscle tissue 30 becomes ischemic or otherwise damaged. Further, because the arterial blood flow is reduced, the venous blood flow exiting from the local vein 21 is likewise reduced. Other branch veins 22 located at different regions along the heart 10 can continue to receive blood flow, thereby creating a supply of venous blood flow exiting through the coronary sinus 20. In some implementations, the coronary sinus occlusion device 120 can be delivered into the coronary sinus 20 and thereafter activated to intermittently occlude the coronary sinus 20 (FIG. 3). Such an occlusion can cause the venous blood flow to be redistributed to the local vein 21 and then into the portion of heart muscle tissue 30 that suffers from a lack of blood flow due to the blockage or reduced flow 35 in the coronary artery and microcirculation 40. As such, the ischemic or otherwise damaged heart muscle tissue 30 can be treated with the redistributed venous blood flow so that the heart muscle tissue 30 receives an improved supply of nutrients.

Referring back to FIGS. 2-3, the coronary sinus occlusion device 120 is deployed into the coronary sinus 20 before the arterial blockage 35 is repaired or removed to restore normal coronary arterial blood flow. However, in alternative implementations, the arterial blockage 35 can be repaired or removed immediately before or contemporaneously during use of the coronary sinus occlusion device 120 to occlude the coronary sinus 20.

Referring to FIGS. 1-3, in some implementations, the heart treatment system 100 can include additional structural components. For example, the distal portion 121 of the coronary sinus occlusion device 120 that is positioned in the coronary sinus 20 can include an occluding portion 122. In the implementations illustrated in FIGS. 2 and 3, the occluding portion 122 is an expandable member in the form of an inflatable balloon device. The expandable member is insertable into the coronary sinus 20 and expandable to occlude at least the portion of the coronary sinus 20. The occluding portion 122 can be activated to place the coronary sinus occlusion device 120 in the occluding position (FIG. 3) to occlude the coronary sinus 20 and thereby cause redistribution of the venous blood into the heart muscle tissue 30 that is damaged due to a lack of arterial blood flow. Simultaneously, an increase in venous pressure translates through the unblocked portion of the microcirculation into an increase in arterial pressure, which results in activation of collateral flow (where present) from arterial side into the deprived portions of the myocardium. As described in more detail below; the occluding portion 122 can be in fluid communication with an internal lumen of the coronary sinus occlusion device 120, which is in turn in communication with a pneumatic subsystem of the control system 140 (see FIG. 1). The control system 140 accordingly can be employed to inflate or deflate the occluding portion 122 in the coronary sinus.

The distal portion 121 also includes one or more distal ports 129 that are positioned distally forward of a distal end of the occluding portion 122. In the implementations illustrated in FIGS. 2 and 3, the distal ports 129 extends distally forward of a distal end of the occluding portion 122. A majority or all of the distal ports face in a generally radially outward direction and are substantially uniformly spaced apart from one another along the circumference of the distal tip.

Figure 5:
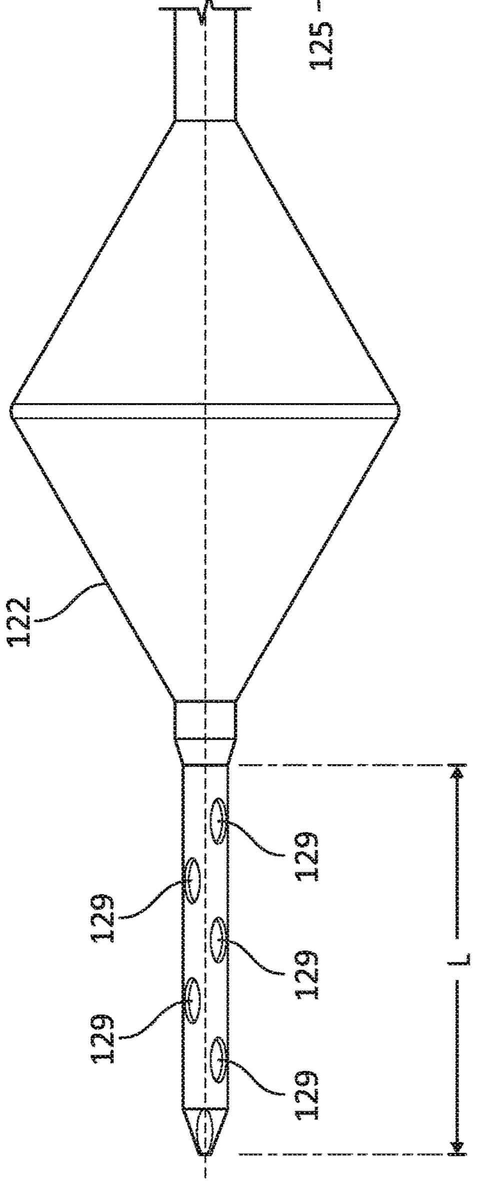
FIG. 5 is a front view of a distal portion of a coronary sinus occlusion device.
Figure 6:
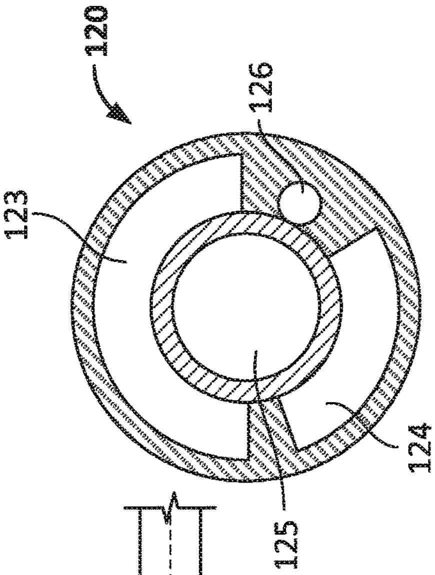
FIG. 6 is a cross-sectional view of a catheter of a coronary sinus occlusion device.

Referring now to FIGS. 4-6, the coronary sinus occlusion device 120 carries the occluding portion 122 along its distal portion 121 while a proximal hub 132 is arranged along a proximal portion 131. As previously described, the proximal hub 132 serves as the connection interface between a number of fluid or sensor lines and the corresponding lumens extending through the coronary sinus occlusion device 120. In the example shown in FIGS. 4-6, lines 133, 134 and lumens 123, 124 are for fluid, and a line 135 and a lumen 125 are for a sensor device.

As previously described, the system 100 can include the guide member 110 that is used to direct the coronary sinus occlusion device 120 through the venous system and into the heart 10. As illustrated in FIG. 4, the guide member 110 can be a guide sheath having a central lumen extending from a proximal end 112 (FIG. 4) to a distal end 111 (FIG. 2). As discussed in this disclosure, the guide member 110 can be equipped with a steering mechanism (e.g., steel cables, a shape memory element, or the like) so that the practitioner can more readily advance the guide member 110 through the venous system and into the right atrium.

Still referring to FIGS. 4-5, the occluding portion 122 of the coronary sinus occlusion device 120 can include an expandable member in the form of an inflatable balloon device having a predetermined shape when in the inflated condition. The occluding portion 122 includes a first conical portion narrowing down toward the distal direction, a second conical portion narrowing down toward the proximal direction, and a small generally cylindrical rim portion which is arranged between the conical portions. The narrowed ends of each of the conical portions are connected with the catheter 127 to provide a seal that prevents gas leakage from the occluding portion 122. In the inflated condition, the diameter of the occluding portion 122 in the region of the cylindrical rim portion is, for example, between about 12 mm and about 40 mm, and preferably about 35 mm. The longitudinal length of the balloon device is, for example, between about 20 mm and about 30 mm. In some implementations, the coronary sinus occlusion device 120 includes one or more marker bands positioned inside or outside of the occluding portion 122 to be rendered visible during an interventional procedure by suitable imaging processes. The shape of the occluding portion 122 may vary in implementations, and may conform to the shape of the anatomy in which the occluding portion 122 is positioned. The occluding portion may be anchored in position within the anatomy.

Referring to FIG. 6, the shaft of the coronary sinus occlusion device 120 extending distally from the proximal hub 132 can include multiple lumens 123, 124, 125, and 126. In this implementation, the ring segment-shaped lumen 123 serves to supply and discharge fluid (e.g., helium gas in this implementation) for inflating and evacuating the occluding portion 122. In the implementations represented by FIG. 6, the lumens 124, 125, and 126 can be used for one or more sensor lines to measure one or more hemodynamics parameters to generate sensors data signals.

The ring segment-shaped lumen 124 can communicate with the interior of the occluding portion 122 and, as discussed in this disclosure, can serve to measure the fluid pressure within the occluding portion 122. In implementations, the lumen 124 and the lumen 123 can have similar dimensions. As further discussed in this disclosure, the central lumen 125 can be employed for measuring the coronary sinus pressure. The central lumen 125 is in fluid communication with the distal ports 129 of the catheter 127 so that the blood pressure in the coronary sinus is transferred to the fluid-filled path extending through the central lumen 125 and to the pressure sensor device 136 (FIG. 1). Alternatively, a miniature pressure sensor can be positioned immediate adjacent to the distal ports 129 such that a sensor wire (e.g., electrical or optical) extends through the central lumen 125 for communication with the control system 140 (FIG. 1). The shaft of the coronary sinus occlusion device 120 includes a fourth lumen 126. One or more additional sensors or sensor wires can be positioned in this fourth lumen.

As illustrated in FIG. 5, the distal ports 129 of the coronary sinus occlusion device 120 are arranged distally forward of the distal end of the occluding portion 122 and are oriented to face generally radially outward from the end of the coronary sinus occlusion device 120. In the depicted implementations, the distal ports 129 and a flexible elongate shaft portion carrying the distal ports 129 can extend for a longitudinal length that is greater than the longitudinal length of the occluding portion 122 so that the distal ports 129 of the coronary sinus occlusion device 120 can be configured to accurately measure pressure in the coronary sinus 20 even if a portion of the distal end abuts against the wall of the coronary sinus or any other vessel. In this implementation, the distal ports 129 include three or more ports that are evenly spaced apart along the flexible elongate shaft portion and along a tapered tip, thereby enabling the fluid pressure in the coronary sinus to be applied into one or more of the ports 129 even if some of the ports 129 are positioned against a wall of the coronary sinus.

The system 100 can include one or more sensors for generating sensor data signals and for determining an indicator value based on at least the sensor data signals. As discussed in this disclosure, the determined indicator value can be computed based on at least a measured value indicative of a hemodynamics parameter, such as, for example, a fluid pressure (e.g., the coronary sinus pressure), a fluid conductance, a fluid temperature (e.g., using a temperature sensor positioned near the distal ports 129 and connected to the control system 140 via the sensor line 135), a volume or mass flow rate or rate of change thereof (e.g., using a flow sensor positioned near the distal ports 129 and connected to the control system 140 via the sensor line 135), a displacement of the coronary sinus vessel (e.g., using an ultrasound or optical measuring device to detect the microvascular perfusion), a quantitative flow ratio value computed for microvascular resistance 20 (e.g., using angiographic imaging techniques and computation fluid dynamics principles), a microvascular resistance 20 (e.g., using angiographic imaging techniques), or another parameter indicative of hemodynamic performance of the heart (e.g., intra-coronary sinus or other intra-vessel electrocardiogram (ECG), contractility measurements, or the like).

Referring to FIGS. 4-5, the distal ports 129 can be in fluid communication with one or more lumens 123, 124, 125, 126 (FIG. 6) extending through the coronary sinus occlusion device 120 for the fluid or sensor lines 133, 134, 135. One or more of the lumens can be fluid lumens, and one or more of the lumens can be sensor lumens. Each of the sensor lumens can provide a sensor that is proximate the distal portion 121 and that is configured to generate sensor data signals indicative of at least one hemodynamics parameter. As discussed in this disclosure, the at least one hemodynamics parameter can be monitored via a sensor in communication with the distal ports 129.

Figure 7:
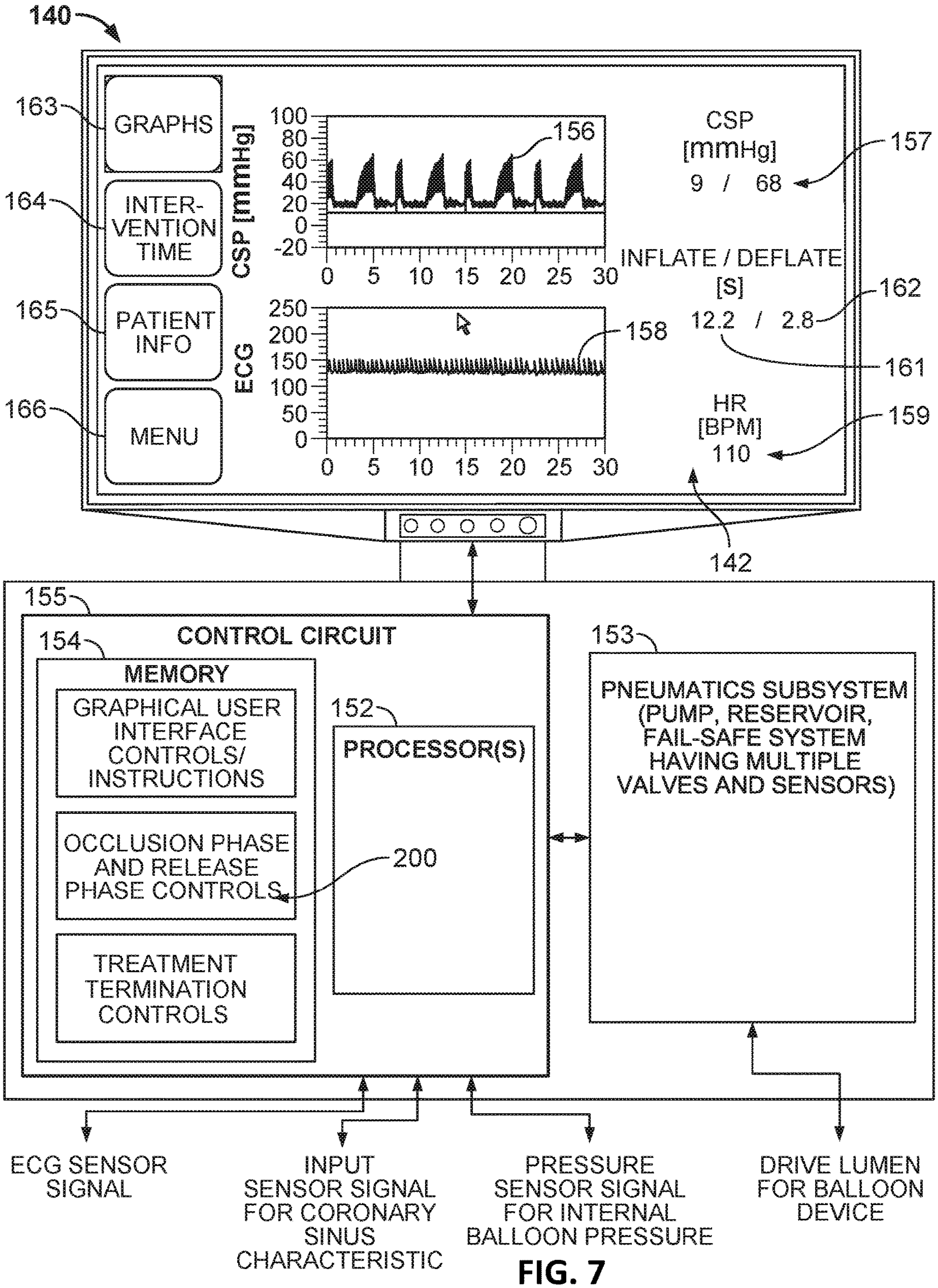
FIG. 7 is a diagram of a control system of a heart treatment system.

Still referring to FIGS. 4-5, the proximal hub 132 of the coronary sinus occlusion device 120 serves to connect the fluid or sensor lines 133, 134, and 135 with the portion of the coronary sinus occlusion device 120 that extends into the patient's venous system. For example, the first line 133 extending between the control system 140 and the proximal hub 132 can include a fluid line through which pressurized fluid (e.g., helium, another gas, or a stable liquid) can be delivered to activate the one or more components of the distal portion 121 (e.g., to expand the expandable member or to inflate the inflatable member). The fluid line 133 is connected to a corresponding port 143 of the control system 140 (e.g., the drive lumen port in this implementation) so that the line 133 is in fluid communication with a pneumatic subsystem 153 housed in the control system 140 (as shown in FIG. 7). The proximal hub 132 joins the first line 133 with a balloon control lumen 123 (FIG. 6) extending through the coronary sinus occlusion device 120 and to the occluding portion 122.

In another example, the second line 134 extending between the control system 140 and the proximal hub 132 includes a balloon sensor line that is in fluid communication with the interior of the occluding portion 122 to measure the fluid pressure within the occluding portion 122. The proximal hub 132 joins the second line 134 with a balloon control lumen 123 (FIG. 5) extending through the coronary sinus occlusion device 120 and to the occluding portion 122. The pressure of the occluding portion 122 can be monitored by an internal control circuit 155 (FIG. 7) of the control system 140 as part of a safety feature that is employed to protect the coronary sinus 20 from an overly pressurized balloon device. The balloon sensor line 134 is connected to a corresponding port 144 of the control system 140 so that a pressure sensor arranged within the control system 140 can detect the fluid pressure in or near the occluding portion 122. Alternatively, the pressure sensor can be arranged in the distal portion 121 or the in the proximal hub 132 such that only a sensor wire connects to the corresponding port 144 of the control system 140.

The proximal hub also connects with a third line 135 extending from the control system 140. As previously described, the third line can serve as the sensor line that is employed to communicate an input signal (as described above) to the control system 140. In this particular implementation, the third line 135 comprises a coronary sinus pressure line that is used to measure the fluid pressure in the coronary sinus both when the occluding portion 122 is inflated and when it is deflated. The proximal hub 132 joins the third line 135 with a coronary sinus pressure lumen 125 (FIGS. 4-5) extending through the coronary sinus occlusion device 120 and to the distal ports 129 that are forward of the occluding portion 122.

In the implementations illustrated in FIG. 4, the sensor line 135 is positioned as a central lumen 125 extending through the coronary sinus occlusion device 120. The sensor line 135 can be configured to communicate an input signal indicative of a measured parameter in the coronary sinus to the control system 140 (FIGS. 1 and 7). For example, the sensor line can be equipped with a sensor (e.g., mounted near the distal ports 129) or otherwise equipped with a communication path between the distal ports 129 and the control system 140. In the implementations represented in FIG. 4, the sensor line 135 of the coronary sinus occlusion device 120 is configured to detect the coronary sinus pressure, which can be accomplished using a pressure sensor positioned near the distal ports 129 or using a fluid-filled path through the sensor line 135. In some implementations, galvanic lines extending through the lumen 126 can connect the sensor to an external device. For example, at least the sensor line 135 is connected to the proximal hub 132 using a Luer lock 137 to maintain the fluid path from the central lumen 125 of the coronary sinus occlusion device 120 to the lumen of the line 135.

In some implementations, the coronary sinus pressure lumen 125 and at least a portion of the third line 135 can operate as fluid-filled path (e.g., saline or another biocompatible liquid) that transfers the blood pressure in the coronary sinus 20 to pressure sensor device 136 along a proximal portion of the third line 135. The pressure sensor device 136 can sample the pressure measurements (which are indicative of the coronary sinus pressure) and output a sensor signal indicative of the coronary sinus pressure to a corresponding port 145 (FIG. 1) of the controller system 140 for input to the internal control circuit 155 (FIG. 7). As described in more detail below; the coronary sinus pressure data are displayed by the graphical user interface 142 in a graph form

156 (refer to FIG. 7) so that a practitioner or other users can readily monitor the trend of the coronary sinus pressure while the coronary sinus 20 is in an occluded condition and in a non-occluded condition. The graph form 156 can present coronary sinus pressure data for one or more cycles of occlusion and release. In some implementations, the graphical user interface 142 of the control system 140 can also output a numeric pressure measurement 157 (refer to FIG. 7) on the screen so that the practitioner can readily view a maximum coronary sinus pressure, a minimum coronary sinus pressure, the mean coronary sinus value, or all values. In alternative implementations, the pressure sensor device 136 can be integrated into the housing of the control system 140 so that the third line 135 is a fluid-filled path leading up to the corresponding port 145, where the internal pressure sensor device (much like the device 136) samples the pressure measurements and outputs a signal indicative of the coronary sinus pressure.

Still referring to FIG. 7, the system 100 can include one or more extracorporeal or intra-cardiac ECG sensors 139 to output ECG signals to the control system 140. In this implementation, the system 100 includes a set of ECG sensor pads 139 (FIG. 1) (e.g., three sensor pads in some implementations) that are adhered to the patient's skin proximate to the heart 10. The ECG sensors 139 are connected to the control system 140 via a cable that mates with a corresponding port 149 (FIG. 1) along the housing of the control system 140. As described in more detail below, the ECG data are displayed by the graphical user interface 142 in a graph form 158 (refer to FIG. 7) so that a practitioner or other user can readily monitor the patient's heart rate and other parameters while the coronary sinus is in an occluded condition and in a non-occluded condition. The graphical user interface 142 of the control system 140 can also output numeric heart rate data 159 (FIG. 7) (based on at least the ECG sensor data on the screen so that the practitioner can readily view the heart rate (e.g., in a unit of beats per minutes). The ECG sensor signals that are received by the control system 140 are also employed by the internal control circuit 155 (FIG. 7) to properly time the start of the occlusion period (e.g., the start time at which the occluding portion 122 is inflated) and the start of the non-occlusion period (e.g., the start time at which the occluding portion 122 is deflated). In addition, the control system can be equipped with additional ECG sensor signals capabilities to monitor the intra-coronary, intra-vessel or intra-coronary sinus electrical ECG activity. These signals can be obtained from the coronary sinus occlusion device 120 measured at one or several locations alongside the catheter 127 or at the distal end where the distal ports 129 are located. Alternatively, or in addition, the ECG activity can be provided from another catheter in the heart such as the intra-coronary ECG from an arterial vessel 40. In implementations, the graphical user interface 142 can present more or fewer graph forms, and the graph forms presented can vary in implementations. The graph forms can represent measured values of any of the parameters described in this disclosure.

The parameter that the sensor measures can vary in implementations. For example, the coronary sinus occlusion device 120 can be configured to communicate at least one input signal indicative of a measured parameter in the coronary sinus. The sensor can be a fluid pressure sensor, and the measured parameter can be a fluid pressure, e.g., a pressure in the coronary sinus 20, or a rate of change in the fluid pressure, e.g., a rate of change of pressure in the coronary sinus 20. In some implementations, the sensor can be a pressure transducer, and the measured parameter can be a wedge pressure associated with the coronary sinus occlusion device 120 or a rate of change of the wedge pressure. The wedge pressure can correspond to a wedge pressure in a portion of the coronary sinus 20 distal to the distal portion 121 or can correspond to an arterial wedge pressure. The sensor can be a temperature sensor positioned near the distal ports 129 and connected to the control system 140 via the lumen 126 or the sensor line 135, and the measured parameter can be a fluid temperature. In implementations in which the sensor is a temperature sensor, the temperature measured by the temperature sensor can correspond to a temperature of a fluid injected into the coronary sinus 20 of the patient or a rate of change of such a temperature. The sensor can be a flow rate sensor, and the measured parameter can be a flow rate in a vascular system of the patient. For example, the flow rate measured by the sensor can be a flow rate in the arterial system of the patient, e.g., a flow rate in a coronary artery of the patient, or a rate of change of such a flow rate, e.g., a rate of change of the flow rate in the coronary artery of the patient. Alternatively, the sensor can measure a flow rate in the venous system of the patient, e.g., a flow rate in a portion of the coronary venous system distal to the distal portion 121 of the coronary sinus occlusion device 120, or a rate of change of such a flow rate, e.g., a rate of change of the flow rate in the portion of the coronary venous system distal to the distal portion 121 of the coronary sinus occlusion device 120.

Rather than being positioned at or proximate the distal ports 129, the sensor, in alternative implementations, can be an external sensor configured to generate the sensor data signals. For example, in some implementations, in addition to or as an alternative to the sensor connected to the sensor line 135, the system 100 (FIG. 1) can include an imaging device (not shown) configured to generate angiographic imagery of at least a portion of the heart 10, e.g., at least a portion of the heart 10 including the coronary sinus 20. The control system 140 can, for example, operate the imaging device to generate the angiographic imagery during the coronary sinus occlusion treatment, and from the angiographic imagery, the control system 140 can determine a value of a quantitative flow ratio in the coronary sinus 20 or a value of a rate of change in the quantitative flow ratio. Alternatively, or additionally, from the angiographic imagery, the control system 140 can determine a value of a microvascular resistance in the coronary sinus 20 or a rate of change of the microvascular resistance.

In implementations, the number of sensors that the system 100 (FIG. 1) includes can vary, and the number of hemodynamics parameters can vary. For example, the system 100 can include a single sensor to measure a hemodynamics parameter, e.g., one of the sensors discussed in this disclosure. In other implementations, the system 100 can include multiple sensors, e.g., two or more sensors discussed in this disclosure. The multiple sensors can include one or more sensors positioned at the distal portion 121, one or more external sensors, or a combination of such sensors. In implementations in which the system 100 includes multiple sensors, sensors can measure values indicative of different hemodynamics parameters or measure values indicative of the same hemodynamics parameter.

Referring now to FIGS. 1 and 7, the control system 140 can be configured to provide automated control of the occluding portion 122 of the coronary sinus occlusion device 120 during a coronary sinus occlusion treatment. As described in this disclosure, the control system 140 can include a computer processor that executes computer-readable instructions stored on a computer memory device intermittently occlude the coronary sinus 20 using a particular process, e.g., the implementations of processes (e.g., algorithms) represented in FIG. 8 or FIG. 9. In particular, the control system 140 can initiate a coronary sinus occlusion treatment and then determine when to terminate the coronary sinus occlusion treatment based on at least the sensor data signals generated during the coronary sinus occlusion treatment, thus controlling the coronary sinus occlusion treatment over a determined treatment duration. The control system 140 can determine indicator values from the sensor data signals and can determine when these indicator values have substantially reached a steady state. In response to determining that the indicator values are substantially in steady state, the control system 140 can terminate the coronary sinus occlusion treatment by releasing the coronary sinus occlusion device 120 from the coronary sinus and ceasing further occlusion phases.

Referring to FIG. 6, the proximal portion 131 of the coronary sinus occlusion device 120 and the control system 140 are positioned external to the patient while the distal portion 121 is advanced into the coronary sinus 20. The proximal portion 131 includes the proximal hub 132 that is coupled to the control system 140 via a set of fluid or sensor lines 133, 134, and 135. As such, the control system 140 can activate or deactivate the occlusion portion 122 at the distal portion 121 of the coronary sinus occlusion device 120 while also receiving one or more sensor signals that provide data indicative of hemodynamics parameters.

Referring to FIG. 7, some implementations of the control system 140 include the internal control circuit subsystem 155 that communicates with the pneumatics subsystem 153. The control circuit subsystem 155 can include one or more processors 152 that are configured to execute various software modules stored on at least one memory device 154. The processors 152 can include, for example, microprocessors that are arranged on a motherboard to execute the control instructions of the control system 140. The memory device 154 can include, for example, a computer hard drive device having one or more discs, a RAM memory device, or the like that stored the various software modules.

In some implementations, the memory device of the control circuit subsystem 155 stores a graphical user interface software module including computer-readable instructions for controlling the graphical user interface 142. These graphical user interface control instructions can be configured to cause the interface 142 (which includes a touch screen display device in this implementation) to display one or more data graphs indicative of values of a hemodynamic parameter determined from sensor data signals generated during a coronary sinus occlusion treatment. The interface 142 provides a practitioner or other users with time-sensitive, relevant data indicative of the progress of a coronary sinus occlusion procedure and the condition of the heart 10. As such, the user can readily monitor the patient's condition and the effects of intermittently occluding the coronary sinus 20 by viewing the graphical user interface while contemporaneously handling the coronary sinus occlusion device 120 and other heart treatment instruments (e.g., angioplasty catheters, stent delivery instruments, or the like).

For example, in the implementations represented in FIGS. 1 and 7, the graphical user interface 142 presents a pressure data graph 156 indicative of the coronary sinus pressure, a coronary sinus pressure numerical data 157, an ECG data graph 158, and a heart rate numerical data 159. The graphical user interface can be configured to display more than two the two graphs 157 and 158 on the screen. For example, in some implementations, the graphical user interface 142 can be configured to contemporaneously display three or four different graphs, such as the coronary sinus pressure numerical data 157, the ECG data graph 158, a third graph that depicts the arterial pressure as a function of time, and a fourth graph that illustrates another data output (e.g., the volume of blood flow).

The pressure data graph 156 can represent one or more occlusion phases. In some implementations, the pressure data graph 156 can represent an entire course of the coronary sinus occlusion treatment. In some implementations, the pressure data graph 156 can be overlaid with a computation of a fitted graph that can be indicative of predicted steady state values for the measured coronary sinus pressure.

Further, the graphical user interface control instructions stored in the control circuit subsystem 155 can be configured to cause the interface 142 to display numeric data of the time periods during which the coronary sinus is in an occluded state and in a non-occluded state. For example, the graphical user interface 142 can provide the occluded time numeric data 161 in units of seconds (e.g., 12.2 seconds as shown in FIG. 7). Also, the graphical user interface 142 can provide the non-occluded time numeric data 162 in units of seconds (e.g., 2.8 seconds as shown in FIG. 7). The graphical user interface control instructions stored in the control circuit subsystem 155 can be configured to cause the interface 142 to display a number of touch screen buttons 163, 164, 165, and 166 that enable the practitioner or other user to select different menu options or to input patient information or other data. In addition, the graphical user interface can be configured to utilize several of the data inputs to display unique determinants of the status of the procedure. This information can guide the user to understand when the heart is improving based on the therapy provided, and thus to understand when to terminate the therapy.

In addition, the graphical user interface control instructions stored in the control circuit subsystem 155 can be configured to cause the interface 142 to display a number of one or more alerts 167, which can be in the form of messages, codes, or recommendations.

While the graphical user interface 142 is described as presenting the pressure data graph 156, alternatively or additionally, the graphical user interface 142 can present one or more data graphs of values of other hemodynamics parameters, as discussed in this disclosure (e.g., flow rate, microvascular resistance, quantitative flow ratio, temperature, etc.).

Still referring to FIG. 7, the pneumatic subsystem 153 of the control system 140 can be configured to promptly inflate or deflate the occluding portion 122 through the fluid line 133 in response to the control circuit subsystem, e.g., based on pressure measured through the sensor line 134. In some implementations, the pneumatic subsystem can include a reservoir containing pressured gas, such as helium or carbon dioxide, and a vacuum pump. The reservoir and the vacuum pump can be controlled by a set of valves and are monitored by a set of pressure sensors that feedback into the control circuit subsystem 155. In such circumstances, the pneumatic subsystem can be configured to inflate or deflate the occluding portion 122 at the distal portion 121 of the coronary sinus occlusion device 120.

Still referring to FIG. 7, an occlusion phase and release phase control module 200 stored on the memory device 154 can include computer-readable instructions that, when executed by one of the processors 152 (such as an embedded PC), causes the pneumatic subsystem 153 to control a duration of a cycle of occlusion and release. Each cycle of occlusion and release can include an occlusion phase and a release phase. The occlusion phase and release phase control module 200 can activate or deactivate the occluding portion 122 to control the cycle, the occlusion phase, and the release phase at selected times. The occlusion phase and release phase control module 200 can control the cycle such that the occlusion phase is sufficiently long and such that the release phase is sufficiently short. The control system 140 can be configured to execute the occlusion phase and release phase control module 200 stored on the memory device 154, which causes the control system 140 to calculate the time periods during which the coronary sinus is in an occluded state and in a non-occluded state. In general, the occlusion phase and release phase control module 200 can control the end of each occlusion phase in order to achieve an optimal clinical benefit of the desired mode of action (e.g., altered venous side blood flow that induces microcirculation in a targeted heart tissue). The occlusion phase and release phase control module 200 can take into account various monitored parameters, and make the timing determinations in real-time, such that timing of each cycle of the method can be appropriate in light of monitored parameters.

The occlusion phase and release phase control module 200 can be configured to store sensor measurements during an occlusion phase, generate a curve fit of the sensor maxima or minima during that same occlusion phase, determine a time derivative of the curve fit line during that same occlusion phase, and use the time derivative of the curve fit line to calculate a time for releasing that occlusion phase. Moreover, the algorithm of the occlusion phase and release phase control module 200 can employ a weighted averaging function that takes previous release times into account when determining whether to release the present occlusion phase, thereby reducing the negative effects (e.g., premature or untimely release of the occlusion phase) that might otherwise result from outlier values input from the sensor line 135. Examples of algorithms for controlling each occlusion phase and release phase are described in U.S. Pat. No. 8,177,704, filed on Dec. 22, 2011, the contents of which are incorporated in its entirety in the present disclosure.

A treatment termination control module 210 is stored on the memory device 154 and can include computer-readable instructions that, when executed by one of the processors 152 (such as an embedded PC), terminates the coronary sinus occlusion treatment by ceasing operation of the pneumatic subsystem 153. The control system 140 can be configured to execute the treatment termination control module 210 stored on the memory device 154 to cause the control system 140 to compute an indicator value, e.g., based on a hemodynamics parameter, from sensor data signals, and compare the indicator value to a threshold value to determine whether a coronary sinus occlusion treatment should be terminated. In particular, the treatment termination control module 210 can allow the control system 140 to control a duration of an overall coronary sinus occlusion treatment so that the coronary sinus occlusion treatment is performed for a sufficient amount of time, for sufficient amount of cycles of occlusion and release phases, or over a sufficient number of occlusion and release phases to achieve an optimal clinical benefit of the desired mode of action (e.g., altered venous side blood flow that induces microcirculation in a targeted heart tissue) and avoid a prolonged or a prematurely terminated coronary sinus occlusion treatment. In particular, the treatment termination control module 210 can terminate the coronary sinus occlusion treatment when the sensor data signals are substantially at steady state, which can indicate that the optimal clinical benefit has been achieved.

Figure 8:
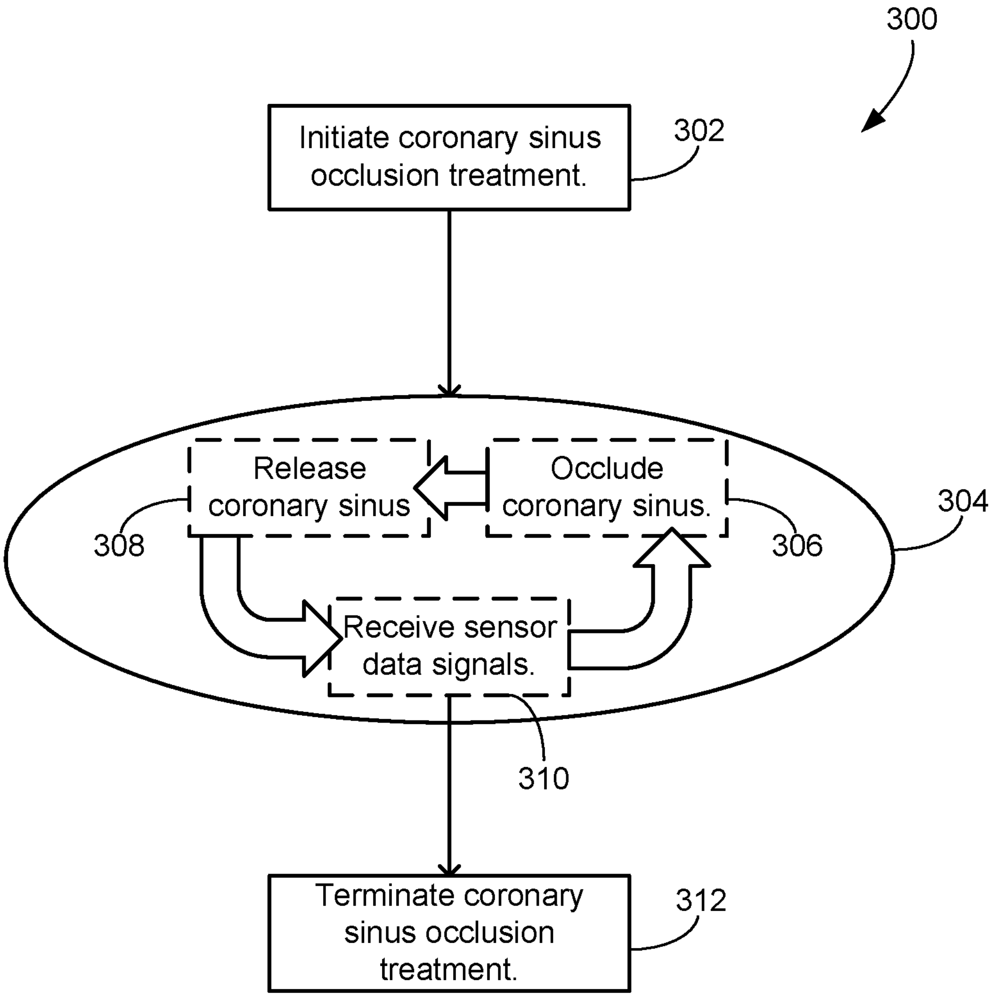
FIGS. 8-9 are flowcharts illustrating algorithms for controlling processes for performing and terminating a coronary sinus occlusion treatment.
Figure 9:
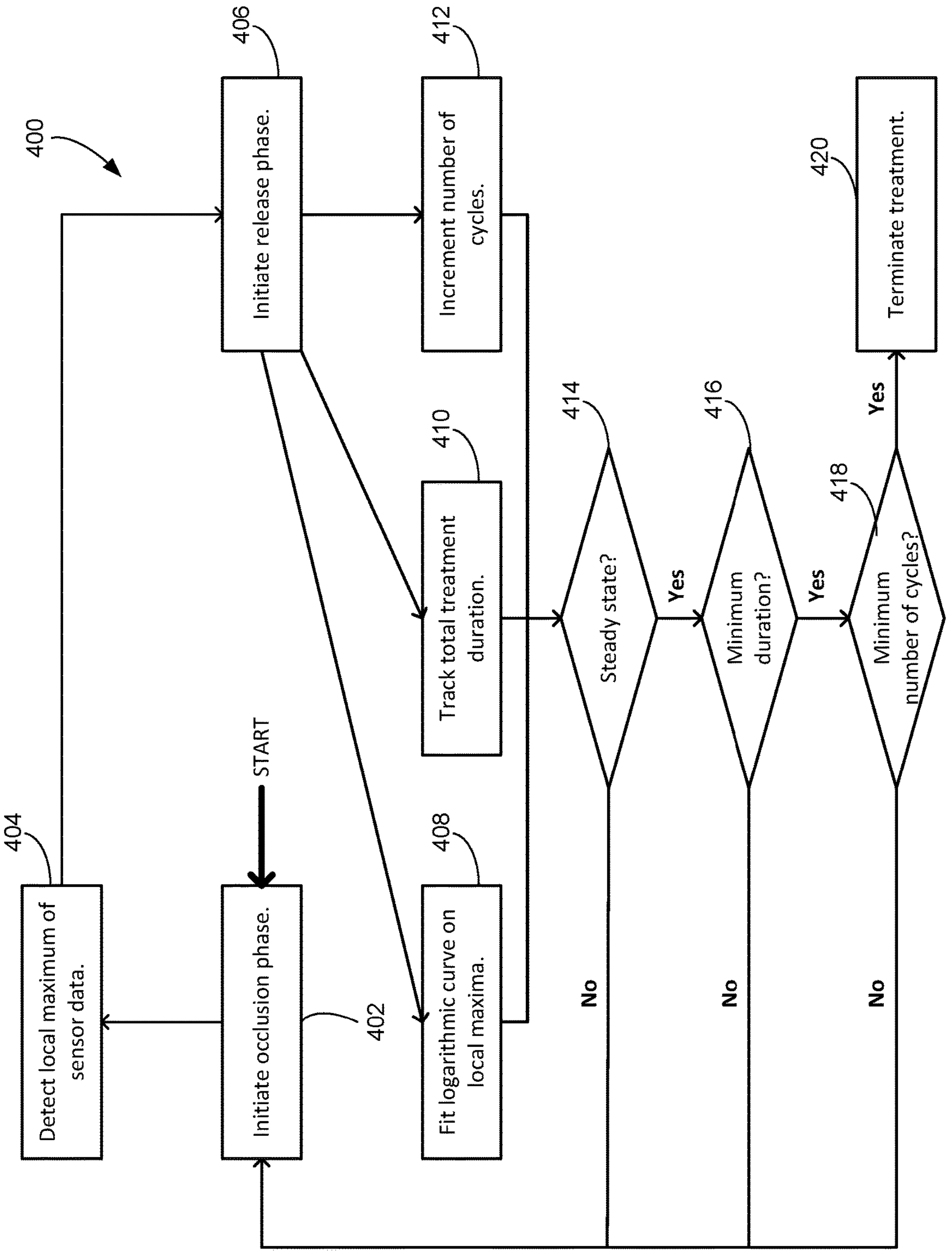

Referring to FIGS. 8 and 9, the treatment termination control module 210 can receive sensor data signals indicative of a hemodynamics parameter of the heart being treated during occlusion phases (e.g., each of which is controlled by the occlusion phase and release phase control module 200), and then control termination of the coronary sinus occlusion treatment in response to comparing a threshold value to an indicator value, e.g., a steady-state indicator value, that is based on the sensor(s) data signals. The determined indicator value based on the sensor data signals can be computed based on one or more measured values of a hemodynamics parameter. For example, in implementations in which the sensor data signals are indicative of a coronary sinus pressure, the indicator value can correspond to a difference between a measured value of coronary sinus pressure and a predicted value of coronary sinus pressure. The measured value of coronary sinus pressure can be a local maximum of the coronary sinus pressure or a local maximum of a rate of change of coronary sinus pressure in an occlusion phase, and the predicted value of coronary sinus pressure can be a predicted local maximum of the coronary sinus pressure or a predicted local maximum of a rate of change of the coronary sinus pressure. The indicator value can be compared to a threshold value to determine whether the sensor data signals are substantially in steady state. An indicator value can be determined for each occlusion phase, and the treatment termination control module 210 can control the pneumatic subsystem 153 to terminate the coronary sinus occlusion treatment when a comparison of the indicator value with the threshold value indicates that the multiple occlusion phases are substantially in steady state.

Example Processes

Referring to FIGS. 8 and 9, example processes 300, 400 illustrate algorithms for controlling a coronary sinus occlusion treatment over a determined duration and terminating the treatment based on the determined duration. These processes can be performed using the system 100 discussed in this disclosure. Alternatively, or additionally, one or more of the operations of the processes 300, 400 can be performed by a human user, e.g., a physician, a nurse, or other healthcare practitioner. Furthermore, while certain operations are described as being performed by the control system 140, in some implementations, operations can be performed, in part or in whole, by one or more controllers separate from the control system 140. The processes 300, 400 are described in connection with the example system 100 shown in FIGS. 1-7.

In the implementations represented in the process 300, a coronary sinus occlusion treatment is initiated, then performed, and then terminated. At an operation 302, the coronary sinus occlusion treatment is initiated. Initiation of the coronary sinus occlusion treatment can involve a manually-provided instruction from a physician to cause the control system 140 to initiate the coronary sinus occlusion treatment. The coronary sinus occlusion treatment is initiated after the coronary sinus occlusion device 120 is positioned in the coronary sinus, e.g., as discussed in connection with FIGS. 1-7. In particular, the distal portion 121 of the coronary sinus occlusion device 120 is positioned in the coronary sinus 20 in the non-occluding position (FIG. 2) such that activation of the occluding portion 122 of the distal portion 121 can cause the coronary sinus 20 to be occluded. Initiation of the coronary sinus occlusion treatment can coincide with initiation of a first occlusion phase (e.g., at a sub-operation 306 as discussed in connection with the operation 304).

At the operation 304, the coronary sinus occlusion treatment is performed. The operation 304 includes sub-operations 306, 308, 310, which can be repeated multiple times during the coronary sinus occlusion treatment.

At the sub-operation 306, the coronary sinus 20 is occluded during an occlusion phase. For example, the control system 140 can transmit one or more control signals to cause the occluding portion 122 to be activated and thereby transition the coronary sinus occlusion device 120 from the non-occluding position (FIG. 2) to the occluding position (FIG. 3). In implementations in which the occluding portion 122 is an expandable member, the occlusion of the coronary sinus 20 occurs as a result of the expandable member being expanded upon activation, thus blocking blood flow across the occluding portion 122. The control system 140 can, for example, operate the pneumatic subsystem 153 to cause the expandable member to expand.

At the sub-operation 308, the coronary sinus occlusion 20 is released during a release phase. For example, the control system 140 can transmit one or more control signals to cause the occluding portion 122 to be deactivated and thereby transition the coronary sinus occlusion device 120 from the occluding position (FIG. 3) to the non-occluding position (FIG. 2). In implementations in which the occluding portion 122 is an expandable member, the release of the coronary sinus occlusion device 120 from the coronary sinus 20 occurs as a result of the expandable member being contracted upon deactivation, thus allowing blood flow through the coronary sinus 20. The control system 140 can, for example, operate the pneumatic subsystem 153 (e.g., deactivate the pneumatic subsystem 153) to cause the expandable member to contract.

At the sub-operation 310, sensor data signals are received by the control system 140. The sensor data signals, as discussed in this disclosure, can vary in implementations. In particular, the sensor used to generate the sensor data signals can vary in implementations, and the particular hemodynamics parameter that the sensor data signals represent can vary implementations. In the implementations illustrated in FIGS. 1-7, the system 100 includes the pressure sensor device 136 (shown in FIG. 1). The pressure sensor device 136 can thus generate the sensor data signals indicative of the coronary sinus pressure, and the control system 140 can receive the sensor data signals.

The sub-operations 306, 308, 310 can be repeated until the control system 140 determines that the coronary sinus occlusion treatment should be terminated. For example, the initiation of the coronary sinus occlusion treatment can correspond to an initiation of a first occlusion phase, e.g., at the sub-operation 306. After the occlusion phase, a release phase occurs. The occlusion phase and the release phase of the sub-operations 306, 308 are then repeated. In particular, at the sub-operation 306, the coronary sinus occlusion device 120 is operated to intermittently occlude the coronary sinus 20 during multiple occlusion phases of the coronary sinus occlusion treatment, and then at the sub-operation 308, the coronary sinus occlusion device 120 is further operated to release the coronary sinus occlusion device 120 following each intermittent occlusion of the coronary sinus 20 during the coronary sinus occlusion treatment.

The repeated occlusion and release phases occur until the control system 140, based on the sensor data signals received at the sub-operation 310, determines that the coronary sinus occlusion treatment may be terminated, unless the user would like to extend the therapy duration. At the sub-operation 310, the sensor data signals received at the control system 140 correspond to sensor data signals indicative of a hemodynamics parameter as measured during the occlusion phases of the sub-operation 306. At the sub-operation 310, upon receiving the sensor data signals, the control system 140 checks whether the coronary sinus occlusion treatment should be terminated based on an indicator value computed based on the sensor data signals. The indicator value, for example, can be computed based on values of a hemodynamic parameter represented by the sensor data signals. The indicator value can be based on one or more values indicative of a hemodynamics parameter. The indicator value can then be compared to a threshold value to determine whether the coronary sinus treatment should be terminated.

Further examples of how the control system 140 determines that the coronary sinus occlusion treatment should be terminated are discussed in connection with the process 400 illustrated in FIG. 9. FIG. 9 represents specific implementations in which the indicator value corresponds to a difference between a measured value of a hemodynamics parameter and a predicted value of the hemodynamics parameter. The measured value, as discussed in connection with FIG. 9 can correspond to a local maximum of the coronary sinus pressure.

The predicted value can be a predicted local maximum computed based on a generalized linear model applied to multiple measured values of the hemodynamics parameter. For example, the predicted value can correspond to a value predicted from a logarithmic fit over multiple measured values of the hemodynamics parameter(s).

The threshold value can correspond to a threshold difference between the local maximum and the predicted local maximum that would indicate that maximum coronary sinus pressure values represented in the sensor data signals are substantially in steady state. As discussed in this disclosure, other predicted values and threshold values are possible in implementations.

Finally, at the operation 312, the coronary sinus occlusion treatment is terminated based on the indicator value, e.g., comparing the indicator value to the threshold value. In some implementations, an end of the final occlusion phase corresponds to the termination of the coronary sinus occlusion treatment. At the end of the final occlusion phase, the control system 140 can determine that further occlusion phases may not be necessary to achieve the optimal clinical benefit. The control system 140 terminates the coronary sinus occlusion treatment by maintaining the coronary sinus occlusion device 120 in the non-occluding position (FIG. 2). After the coronary sinus occlusion treatment is terminated, the coronary sinus occlusion device 120 can be removed from the coronary sinus 20.

FIG. 9 illustrates specific implementations for terminating a coronary sinus occlusion treatment. In the process 400 of FIG. 9, the hemodynamics parameter that is measured and predicted is a coronary sinus pressure. The measured values and predicted values of the coronary sinus pressure are used to determine whether to terminate the coronary sinus occlusion treatment.

At the operation 402, the occlusion phase is initiated. In particular, the control system 140 can operate the system 100 using the methods discussed in connection with the sub-operation 306.

Referring to FIG. 9, in some implementations, at the operation 404, a local maximum of sensor data is detected. For example, the control system 140 can receive the sensor data signals (e.g., similar to the sub-operation 310), and the sensor data signals can be indicative of a hemodynamics parameter measured during the occlusion phase. The control system 140 can determine a local maximum of a measured value represented by the sensor data signals. The local maximum can correspond to the measured value described in connection with the sub-operation 310 of FIG. 8.

Figure 10:
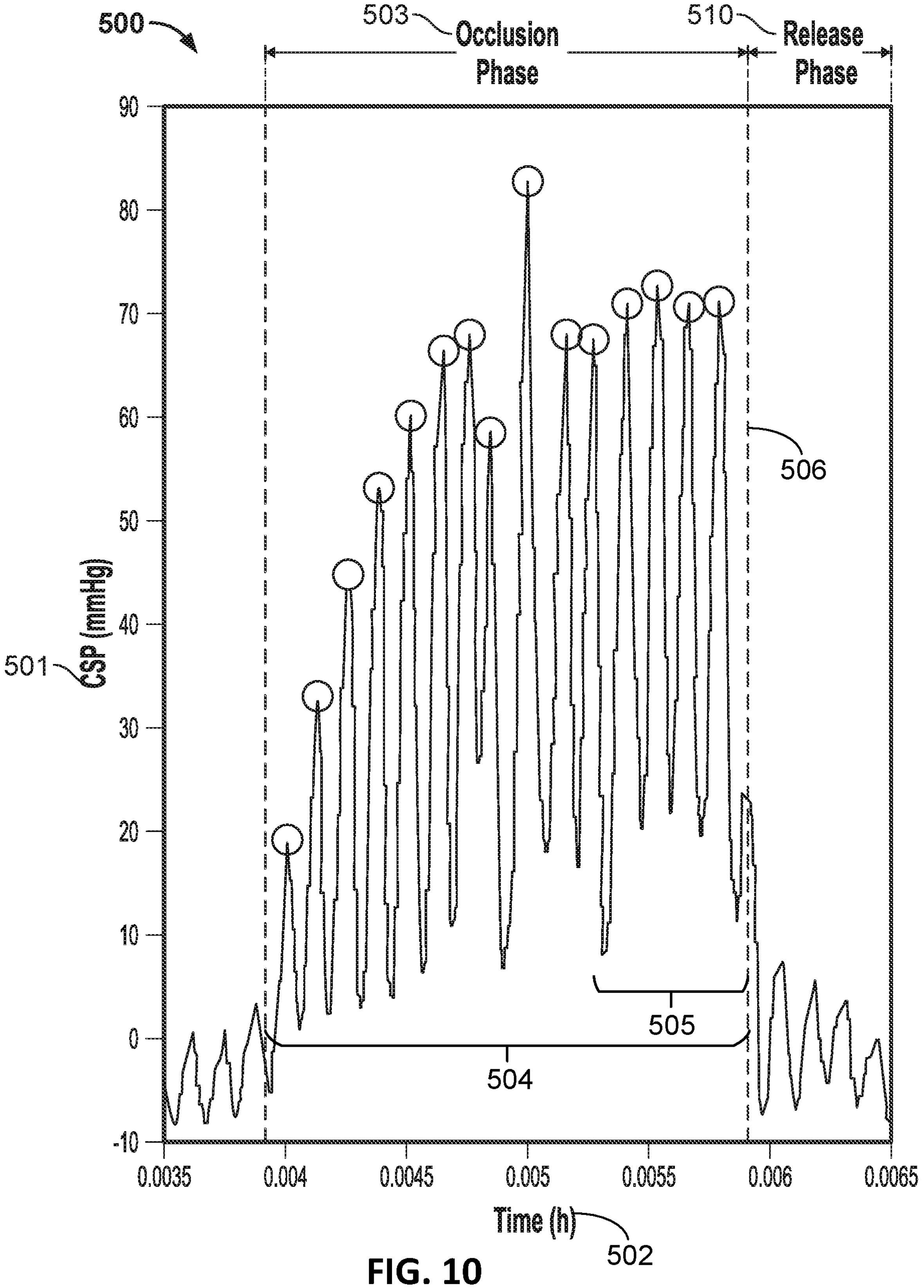
FIG. 10 is a diagram of measured values of a hemodynamics parameter during an occlusion phase and a release phase of a coronary sinus occlusion treatment.

The local maximum of the measured value can be computed in various ways depending on the implementation. FIG. 10 illustrates an example representation 500 of sensor data signals received by the control system 140. The sensor data signals are a series of real-time measurements of coronary sinus pressure 501 at various times 502, including during an occlusion phase 503 and a release phase 510. The occlusion phase 503 (e.g., initiated at the operation 402) occurs over a period of time 504. The sensor data signals are indicative of measured values over this period of time 504. As shown in FIG. 10, the coronary sinus pressure increases during the occlusion phase 503 when the coronary sinus occlusion device 120 is placed in the occluding position (FIG. 3) and then decreases in the release phase 510 when the coronary sinus occlusion device is placed in the non-occluding position (FIG. 2). The local maximum for the occlusion phase 503 can correspond to a maximum value during this period of time. In some implementations, the local maximum can correspond to a maximum value during a sub-period of the period of time 504 for the occlusion phase. For example, the sub-period can be an end period 505 starting at some point during the period of time and ending at an end 506 of the period of time 504. The end period 505 can have a duration between, for example, 0.5 and 3 seconds (e.g., between 0.5 and 1 second, 0.5 and 1.5 seconds, 0.5 and 2 seconds, 0.5 and 2.5 seconds, 1 and 2 seconds, 1 and 2.5 seconds, 1.5 and 2 seconds, 1.5 and 2.5 seconds, etc.).

Referring back to FIG. 9, at the operation 406, a release phase is initiated. In particular, the control system 140 can operate the system 100 using the methods discussed in connection with the sub-operation 310. In some implementations, the control system 140 can determine when to initiate the release phase based on the measured values of the sensor data signals during the occlusion phase initiated at the operation 402. For example, as discussed in this disclosure, the occlusion phase and release phase control module 200 can release the occlusion phase (e.g., deflate the inflatable balloon device of the occluding portion 122) in the coronary sinus 20 in response to the sensor data (e.g., coronary sinus pressure measurements) generated during the same occlusion phase.

Figure 11:
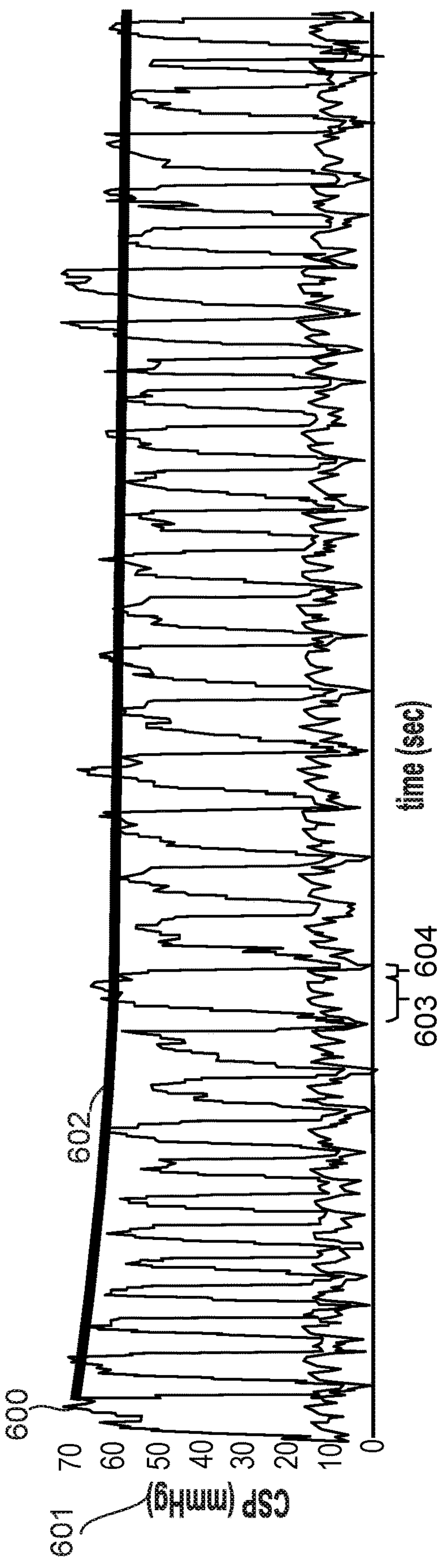
FIG. 11 is a diagram of examples of measured and predicted values of a hemodynamics parameter during multiple occlusion and release phases of a coronary sinus occlusion treatment.

At the operation 408, a logarithmic curve is fitted on local maxima detected at each instance of the operation 404, after processing the data through a high-pass filter (e.g. to remove breathing effects). In particular, the coronary sinus occlusion treatment involves multiple occlusion phases, each of which is proceeded by a corresponding release phase. FIG. 11 illustrates a representation 600 of coronary sinus pressure measurements that are collected over multiple occlusion and release phases. As shown in FIG. 11, each occlusion phase (e.g., occlusion phase 603) is followed by a corresponding release phase (e.g., release phase 604). The coronary sinus pressure 601 increases during the occlusion phase and then decreases during the release phase. The representation 600 shows multiple occlusion and release phases. In other words, the representation 600 shows the sensor data signals collected over multiple instances of the operations 402, 404, 406. Overlaid on the representation 600 of the coronary sinus pressure measurements is a logarithmic curve 602 fitted based on local maxima detected at each of the occlusion phases, e.g., collected at the operation 404 during each corresponding occlusion phase.

In some implementations, at the operation 412, a number of cycles of the occlusion and release phases is incremented. As discussed below in connection with the operations 414, 416, 418, one or more of the logarithmic curve fitted at the operation 408, the total duration of the coronary sinus occlusion treatment determined at the operation 410, or the total number of cycles determined at the operation 412 can be used to determine whether to terminate the coronary sinus treatment. The operations 408, 410, 412 represent operations to determine specific values that are in turn used to determine at the operations 414, 416, 418 whether certain conditions are satisfied for terminating the coronary sinus occlusion treatment.

The operation 414 is performed to determine whether the local maximum detected at the operation 404 corresponds to a substantially steady state value. If the local maximum is a substantially steady state value, then the control system 140 can terminate the treatment at the operation 420 or, in some implementations, optionally perform the operations 416 and/or 418 to determine whether one or more other conditions are satisfied for terminating the coronary sinus occlusion treatment. If the local maximum is not a substantially steady state value, the control system 140 can proceed to initiate further occlusion and release phases, e.g., by performing the operations 402, 404, 406 again. In other words, the control system 140 can continue performing the coronary sinus occlusion treatment.

In the implementations represented in FIG. 9, the local maximum corresponds to a measured value that was determined at the most recent or the last instance of the operation 404. Typically, at the operation 414, multiple occlusion phases have previously occurred, with each of the multiple occlusion phases providing corresponding local maximum at the operation 404. The local maximum at the most recent instance of the operation 404 is used as the basis for comparing a threshold value for determining whether the coronary sinus occlusion treatment should be terminated.

The threshold value can be a threshold difference between the measured value and a predicted value. The predicted value is computed based on one or more previously measured values. For example, a generalized linear model, e.g., logarithmic regression, or other appropriate curve for the sensor signals, can be used to determine a predicted value of the coronary sinus pressure. A difference between the local maximum detected at the most recent instance of the operation 404 and a value predicted by the logarithmic curve 602 determined at the operation 408 can be computed. This difference can correspond to the indicator value used at the sub-operation 310 to determine whether the coronary sinus occlusion treatment should be terminated. The logarithmic curve 602 can provide a predicted value for the local maximum if a subsequent occlusion phase were to be initiated. The difference between the most recent local maximum value detected at the operation 404 and the value predicted using the logarithmic curve 602 can be used to determine whether the local maximum detected at the most recent instance of the operation 408 indicates that the local maxima values are substantially in steady state. This difference can then be compared to a threshold value. The threshold value is a threshold difference between the measured value and the predicted value. In implementations, the threshold value can be a percent difference. The percent difference can be, for example, between 0.1% and 10% (e.g., between 0.1% and 5%, 0.1% and 2.5%, 0.1% and 1%, 1% and 10%, 1% and 5%, 1% and 3%, 1% and 2.5%, etc.). The threshold value can be a constant value or can be selected based on different factors. In some implementations, the control system 140 determines the threshold value based on a condition of a patient, a type of coronary sinus occlusion treatment being administered, or other factors that can affect the target clinical effect of the coronary sinus occlusion treatment. In some implementations, rather than computing predicted value, the control system 140 compares the value to a previous value, e.g., the value measured in the immediately preceding occlusion phase or an earlier value.

In some implementations, the operation 416 is optionally performed to determine whether a minimum duration of the coronary sinus occlusion treatment has elapsed. For example, a total elapsed duration of the coronary sinus occlusion treatment can be tracked at the operation 410, and at the operation 416, this total elapsed duration can be compared to a threshold duration. If the total elapsed duration is less than the threshold duration, the control system 140 can continue administering the coronary sinus occlusion treatment, e.g., by performing the operations 402, 404, 406 again. If the total elapsed duration is no less than the threshold duration, the control system 140 can terminate the coronary sinus occlusion treatment at the operation 420 or, in some implementations, can perform the operation 418 to determine whether the number of cycles initiated is no less than a threshold amount.

In some implementations, the operation 418 is optionally performed to determine whether a minimum number of cycles of the occlusion and release phases have occurred. A cycle includes an occlusion phase and a release phase. A total number of cycles of the occlusion and release phases is tracked at the operation 412, and this total number of cycles is compared to a threshold number of cycles at the operation 418. If the total number of cycles is less than the minimum number of cycles, the control system 140 can continue administering the coronary sinus occlusion treatment, e.g., by performing the operations 402, 404, 406 again. If the total number of cycles is no less than the minimum number of cycles, the control system 140 can terminate the coronary sinus occlusion treatment at the operation 420.

Further Alternative Implementations

A number of implementations have been described. Nevertheless, it will be understood that various modifications can be made.

The systems and methods are described in this disclosure as being used to occlude a portion of a coronary sinus. In implementations, other portions of the heart anatomy in addition to the coronary sinus can also be occluded during the occlusion phase. For example, a great cardiac vein of the heart can be occluded during the occlusion phase. The coronary sinus occlusion device 120 can occlude at least the portion of the coronary sinus 20 and also occlude a portion of the great cardiac vein of the heart.

While the system 100 is described as including the one or more sensors, in other implementations, the one or more sensors may be separate from the system 100. The one or more sensors can include devices that can operate independently from the system 100. While sensor lines for the one or more sensors have been described as being positioned in a venous system, in other implementations, one or more of the sensor lines can be positioned in an arterial system of the heart. In implementations, not all of the operations 408, 410, 412, 414, 416, 418 are performed. For example, in some implementations only the operations 408, 414 are performed, e.g., to determine whether values of a hemodynamics parameter, for determining whether to terminate the coronary sinus occlusion treatment. In other implementations, the operations 408, 410, 414, 416 are performed such that the control system 140 checks two or more conditions before terminating the coronary sinus occlusion treatment, for example, a steady state condition and a minimum duration condition.

While the operation 404 in the process 400 is described above as an operation to detect the local maximum of the hemodynamics parameter, e.g., the coronary sinus pressure, the value of the hemodynamics parameter that is detected at the operation 404 may vary in implementations. For example, the value can correspond to an average value in a period of time during an occlusion phase, e.g., the period of time 504 or the end period 505 as shown in FIG. 10. The control system 140 can compute the average value based on each of the values of the hemodynamics parameter as measured during the selected period of time.

In some implementations, the indicator value used to determine whether the coronary sinus occlusion treatment should be terminated is described as a difference between a measured value of a hemodynamics parameter and a predicted value of the hemodynamics parameter. In other implementations, the indicator value can be another value computed based on the measured value and the predicted value, such as a sum, an average, or another mathematical operation using both the measured value and the predicted value. The predicted value, in implementations in which a generalized linear model is used, can be computed based on multiple measured values. In some implementations, the indicator value can be computed based on multiple measured values. For example, the indicator value can represent an average of multiple measured values.

While the hemodynamics parameter is described as being a coronary sinus pressure in the process 400, the hemodynamics parameter may vary in implementations. As discussed in connection with FIGS. 1-7, the heart treatment system 100 can include one or more sensors distinct from a pressure sensor for measuring a coronary sinus pressure. The one or more sensors can measure a hemodynamics parameter distinct from the coronary sinus pressure. The hemodynamics parameter can be, as discussed in this disclosure, a coronary wedge pressure, a flow rate in a coronary artery, a flow rate in a coronary venous system, a density or viscosity of a blood in the coronary venous system, a temperature of a fluid injected into the coronary sinus, a quantitative flow ratio, a microvascular resistance, another hemodynamics parameter that is indicative of the coronary sinus pressure or represents a clinical effect of the coronary sinus occlusion treatment, or a rate of change of any of these parameters. In some implementations, the one or more sensors can measure a hemodynamic and other parameters on an arterial side of the heart.

Figure 12:
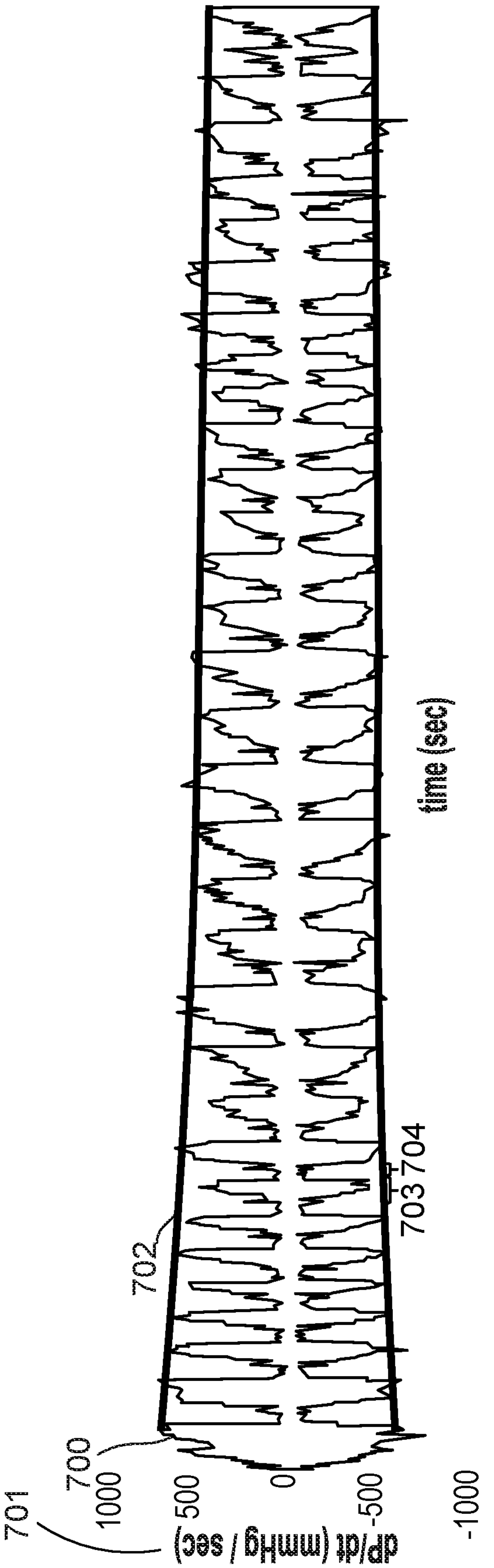
FIG. 12 is a diagram of further examples of measured and predicted values of a hemodynamics parameter during multiple occlusion and release phases of a coronary sinus occlusion treatment.

As discussed in this disclosure, in some implementations, the sensor data signals are indicative of a pressure in the coronary sinus 20. In other implementations, the hemodynamics parameter is the rate of change of the coronary sinus pressure, and the sensor data signals are indicative of a rate of change in the pressure in the coronary sinus 20. FIG. 12 illustrates a representation 700 of sensor data signals indicative of a rate of change of pressure 701 in the coronary sinus 20. Each occlusion phase (e.g., occlusion phase 703) is followed by a corresponding release phase (e.g., released phase 704). The rate of change of pressure is at a local maximum value during each of the occlusion phases. Overlaid on the representation 700 of the rate of change of the coronary sinus pressure measurements is a logarithmic curve 702 fitted based on local maxima detected at each of the occlusion phases. For example, instead of or in addition to detecting the local maximum of the coronary sinus pressure at the operation 404 and fitting a logarithmic curve over local maxima of the coronary sinus pressure over multiple occlusion phases, the control system 140 detects the local maximum of the rate of change of the coronary sinus pressure and fits a logarithmic curve over local maxima of the rate of change over the multiple occlusion phases. Sensor data signals from the same pressure sensor (e.g., the pressure sensor device 136) can be used for detecting the local maximum of the coronary sinus pressure and the local maximum of the rate of change of the coronary sinus pressure.

The linear model for the measured values can vary in implementations. The linear model can involve a logarithmic fit, for example, when the sensor signals are indicative of coronary sinus pressure. In implementations in which other sensor signals are used, the linear model that is used to determine a fit curve could vary.

In addition, in some implementations, a machine learning model can be applied to In implementations in which multiple hemodynamics parameters are measured during the occlusion phase, the control system 140 can measure a second hemodynamics parameter and correlate this second hemodynamics parameter measured by other sensors of the system 100 to the first hemodynamics parameter, thereby creating a multiple closed loop system for determining when to terminate the coronary sinus occlusion treatment. In some implementations, the indicator value that is compared to the threshold value is computed based on both the measured values for the first and second hemodynamics parameters. By way of example, in the process 400, in addition to measuring the coronary sinus pressure and detecting the local maximum for the coronary sinus pressure at the operation 404, the control system 140 can use one or more sensors for measuring another hemodynamics parameter, such as flow rate, and detecting the local maximum for this other hemodynamics parameter. Both the measured coronary sinus pressure and/or its derivatives, and the other measured hemodynamics parameter(s) can be used to compute an indicator value. When this indicator value is substantially at steady state over multiple occlusion phases, e.g., determined using methods similar to those discussed in connection with the operations 408, 414, the control system 140 can then terminate the treatment at the operation 420.

In some implementations, only one hemodynamics parameter is measured and used to determine when to terminate the coronary sinus occlusion treatment. That parameter can be the coronary sinus pressure, as discussed in connection with the process 400. Alternatively, that parameter can be any of the other hemodynamics parameters discussed in this disclosure. That parameter can be indicative of the coronary sinus pressure. When values of that parameter are determined to be substantially at steady state, the control system 140 can terminate the coronary sinus occlusion treatment.

The operations 312 (FIG. 8) and 420 (FIG. 9) are described as being operations to terminate the coronary sinus occlusion treatment that occur as a result of a condition being satisfied. Specifically, the control system 140 terminates the treatment in response to the steady state condition of a hemodynamics parameter being satisfied. In other implementations, the coronary sinus occlusion treatment is not immediately terminated by the control system 140 in response to the condition being satisfied. Instead, the control system 140 can provide a user prompt to terminate the coronary sinus occlusion treatment. For example, the user prompt can include a recommendation (e.g., using a user interface of the control system 140, such as the graphical user interface 142) to a healthcare professional to terminate the coronary sinus occlusion treatment. The recommendation can be presented on a display of the graphical user interface 142. In some implementations, the user prompt is presented as an indicator light. In some implementations, the user prompt can be provided in combination with an audible alert. The user prompt is provided in place of the operation 420, and then the healthcare professional can manually operate the control system 140 to terminate the coronary sinus occlusion treatment.

In further implementations, the recommendation can include an alert indicating a recommended duration for the coronary sinus occlusion treatment and a total elapsed duration for the coronary sinus occlusion treatment. For example, based on a difference between the measured value and the predicted value of the hemodynamics parameter, the control system 140 can compute a recommended duration of the coronary sinus occlusion treatment and provide an indicator of this recommended duration.

The subject matter and the actions and operations described in this disclosure, e.g., as being performed by the control system 140, can be implemented in digital electronic circuitry, in tangibly-embodied computer software or firmware, in computer hardware, including the structures disclosed in this disclosure and their structural equivalents, or in combinations of one or more of them. The subject matter and the actions and operations described in this disclosure can be implemented as or in one or more computer programs, e.g., one or more modules of computer program instructions, encoded on a computer program carrier, for execution by, or to control the operation of, data processing apparatus. The carrier can be a tangible non-transitory computer storage medium. Alternatively or in addition, the carrier can be an artificially generated propagated signal, e.g., a machine-generated electrical, optical, or electromagnetic signal, that is generated to encode information for transmission to suitable receiver apparatus for execution by a data processing apparatus. The computer storage medium can be or be part of a machine-readable storage device, a machine-readable storage substrate, a random or serial access memory device, or a combination of one or more of them. A computer storage medium is not a propagated signal.

The term "data processing apparatus" encompasses all kinds of apparatus, devices, and machines for processing data, including by way of example a programmable processor, a computer, or multiple processors or computers. Data processing apparatus can include special-purpose logic circuitry, e.g., an FPGA (field programmable gate array), an ASIC (application specific integrated circuit), or a GPU (graphics processing unit). The apparatus can also include, in addition to hardware, code that creates an execution environment for computer programs, e.g., code that constitutes processor firmware, a protocol stack, a database management system, an operating system, or a combination of one or more of them.

A computer program can be written in any form of programming language, including compiled or interpreted languages, or declarative or procedural languages: and it can be deployed in any form, including as a stand-alone program, e.g., as an app, or as a module, component, engine, subroutine, or other unit suitable for executing in a computing environment, which environment may include one or more computers interconnected by a data communication network in one or more locations.

A computer program may, but need not, correspond to a file in a file system. A computer program can be stored in a portion of a file that holds other programs or data, e.g., one or more scripts stored in a markup language document, in a single file dedicated to the program in question, or in multiple coordinated files, e.g., files that store one or more modules, sub programs, or portions of code.

The processes and logic flows described in this disclosure, e.g., the processes 300, 400, can be performed by one or more computers, e.g., of the control system 140, executing one or more computer programs to perform operations by operating on input data and generating output. The processes and logic flows can also be performed by special-purpose logic circuitry, e.g., an FPGA, an ASIC, or a GPU, or by a combination of special-purpose logic circuitry and one or more programmed computers.

Computers suitable for the execution of a computer program can be based on general or special-purpose microprocessors or both, or any other kind of central processing unit. Generally, a central processing unit will receive instructions and data from a read only memory or a random access memory or both. The essential elements of a computer are a central processing unit for executing instructions and one or more memory devices for storing instructions and data. The central processing unit and the memory can be supplemented by, or incorporated in, special-purpose logic circuitry.

Generally, a computer will also include, or be operatively coupled to, one or more mass storage devices, and be configured to receive data from or transfer data to the mass storage devices. The mass storage devices can be, for example, magnetic, magneto optical, or optical disks, or solid state drives. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

The graphical user interface 142 is one example of an interface for interaction with the user. In other implementations, to provide for interaction with a user, the subject matter described in this disclosure can be implemented on one or more computers having, or configured to communicate with, a display device, e.g., a LCD (liquid crystal display) monitor, or a virtual-reality (VR) or augmented-reality (AR) display, for displaying information to the user, and an input device by which the user can provide input to the computer, e.g., a keyboard and a pointing device, e.g., a mouse, a trackball or touchpad. Other kinds of devices can be used to provide for interaction with a user as well: for example, feedback and responses provided to the user can be any form of sensory feedback, e.g., visual, auditory, speech or tactile: and input from the user can be received in any form, including acoustic, speech, or tactile input, including touch motion or gestures, or kinetic motion or gestures or orientation motion or gestures. In addition, a computer can interact with a user by sending documents to and receiving documents from a device that is used by the user: for example, by sending web pages to a web browser on a user's device in response to requests received from the web browser, or by interacting with an app running on a user device, e.g., a smartphone or electronic tablet. Also, a computer can interact with a user by sending text messages or other forms of message to a personal device, e.g., a smartphone that is running a messaging application, and receiving responsive messages from the user in return.

Accordingly, other implementations are within the scope of the claims.

What is claimed is:

1. A system comprising:

a coronary sinus occlusion device operable to occlude at least a portion of a coronary sinus of a heart of a patient; and a control system connectable to the coronary sinus occlusion device and configured to execute computer-readable instructions that perform operations including:

activating the coronary sinus occlusion device to intermittently occlude the coronary sinus during a plurality of occlusion phases of a coronary sinus occlusion treatment, operating the coronary sinus occlusion device to release each intermittent occlusion of the coronary sinus during the coronary sinus occlusion treatment, receiving sensor data signals indicative of a hemodynamics parameter of the heart during the plurality of occlusion phases, comparing a threshold value to an indicator value that is based on the sensor data signals of the plurality of occlusion phases, and terminating the coronary sinus occlusion treatment based on said comparing the threshold value to the value or providing a user prompt on a user interface to terminate the coronary sinus occlusion treatment based on said comparing the threshold value to the indicator value, wherein said terminating the coronary sinus occlusion treatment or providing the user prompt on the user interface to terminate the coronary sinus occlusion treatment is performed in response to a determination that a plurality of indicator values that are based on the sensor data signals of the plurality of occlusion phases are substantially in steady state, the plurality of indicator values comprising the indicator value, wherein the operations include:

predicting a value of the hemodynamics parameter, wherein the indicator value corresponds to a difference between at least one of the plurality of indicator values and the predicted value, wherein the at least one of the plurality of indicator values corresponds to a last indicator value of the plurality of indicator values, and wherein the difference is a percent difference between the at least one of the plurality of indicator values and the predicted value.

2. The system of claim 1, wherein the coronary sinus occlusion device comprises:

an expandable member insertable into the coronary sinus and expandable to occlude at least the portion of the coronary sinus, and a sensor that generates the sensor data signals.

3. The system of claim 2, wherein the sensor is positioned near the expandable member.

4. The system of claim 2, wherein the coronary sinus occlusion device comprises a catheter, and the expandable member and the sensor are positioned on a distal portion of the catheter.

5. The system of claim 2, wherein the sensor is a pressure sensor configured to measure a pressure or a rate of change of the pressure in the coronary sinus.

6. The system of claim 2, wherein the sensor is configured to measure:

a flow rate in a coronary artery of the patient or a rate of change of the flow rate in the coronary artery of the patient;

a flow rate in a coronary venous system distal to a distal end of the coronary sinus occlusion device or a rate of change of the flow rate in the coronary venous system;

a coronary wedge pressure associated with the coronary sinus occlusion device or a rate of change of the coronary wedge pressure;

a density or viscosity of blood in the coronary venous system or a rate of change of the density or viscosity;

a temperature of a fluid injected into a coronary sinus of the patient or a rate of change of the temperature of the fluid;

a quantitative flow ratio of microcirculation or a rate of change of the quantitative flow ratio;

a microvascular resistance in the coronary sinus or a rate of change of the microvascular resistance; or any combination thereof.

7. The system of claim 6, wherein the sensor is a first sensor, the sensor data signals are first sensor data signals, and the coronary sinus occlusion device further comprises a second sensor configured to generate second sensor data signals indicative of a pressure or a rate of change of the pressure in the coronary sinus, and the indicator value is based on the first sensor data signals and the second sensor data signals.

8. The system of claim 1, wherein the coronary sinus occlusion device comprises:

an expandable member insertable into the coronary sinus and expandable to occlude at least the portion of the coronary sinus, a first sensor that generates at least some of the sensor data signals, and a second sensor that generates at least some of the sensor data signals, wherein the first and second sensors are positioned on first and second sides of the expandable member.

9. The system of claim 1, wherein receiving the sensor data signals comprises receiving, from a sensor configured to measure the hemodynamics parameter in an arterial system of the heart, the sensor data signals.

10. The system of claim 1, wherein the sensor data signals are indicative of a pressure or a rate of change of the pressure in the coronary sinus.

11. The system of claim 10, wherein the operations include:

determining the indicator value based on, for each of the plurality of occlusion phases, a maximum value of the pressure or the rate of change of the pressure in the coronary sinus in a period of time during a corresponding occlusion phase.

12. The system of claim 11, wherein, for each of the plurality of occlusion phases, the period of time corresponds to an end period of the corresponding occlusion phase.

13. The system of claim 10, wherein the operations include:

determining the indicator value based on, for each of the plurality of occlusion phases, an average value of the pressure or the rate of change of the pressure in the coronary sinus in a period of time during a corresponding occlusion phase.

14. The system of claim 1, wherein the threshold value is no less than 1 percent and is no more than 5 percent.

15. The system of claim 1, wherein the operations include:

determining the threshold value based on one or more of a condition of the patient or a type of the coronary sinus occlusion treatment.

16. The system of claim 1, wherein the operations include:

after providing the user prompt on the user interface to terminate the coronary sinus occlusion treatment, terminating the coronary sinus occlusion treatment only if at least a duration of the coronary sinus occlusion treatment is no less than a threshold duration.

* * * * *